US005474926A

United States Patent [19]
Harman et al.

[11] Patent Number: 5,474,926
[45] Date of Patent: Dec. 12, 1995

[54] **N-ACETYL-β-GLUCOSAMINIDASE ISOLATED FROM *TRICHODERMA HARZIANUM***

[75] Inventors: Gary E. Harman, Geneva, N.Y.; Matteo Lorito, Salerno, Italy; Antonio Di Pietro, Cordoba, Spain; Christopher K. Hayes, Geneva, N.Y.

[73] Assignee: Cornell Research Foundation, Inc., Ithaca, N.Y.

[21] Appl. No.: 49,390

[22] Filed: Apr. 21, 1993

Related U.S. Application Data

[63] Continuation-in-part of Ser. No. 990,609, Dec. 15, 1992, Pat. No. 5,326,561.

[51] Int. Cl.$^6$ .............................. C12N 9/24; C12N 9/00; C12N 1/14
[52] U.S. Cl. .................. 435/200; 435/183; 435/254.6; 435/945
[58] Field of Search .................. 435/254, 200, 435/254.1, 254.6, 183, 209, 945

[56] References Cited

U.S. PATENT DOCUMENTS

| | | | |
|---|---|---|---|
| 4,477,433 | 10/1984 | Hultman | 435/254 |
| 4,489,161 | 12/1984 | Papavizas | 435/254 |
| 4,751,081 | 6/1988 | Suslow et al. | 424/93 |
| 4,940,840 | 7/1990 | Suslow et al. | 435/172.3 X |
| 5,173,419 | 12/1992 | Harman et al. | 435/209 |
| 5,290,687 | 3/1994 | Suslow et al. | 435/69.1 |

FOREIGN PATENT DOCUMENTS

| | | |
|---|---|---|
| 88/123645 | 11/1989 | Japan. |
| 2-286082 | 11/1990 | Japan. |

OTHER PUBLICATIONS

Tronsmo, A., Aktuelt fra Statens Fagtjeneste for Landbruket 2, 107–113 (1985).
Tronsmo, A., Norwegian Journal of Agricultural Sciences 3:157–161 (1989).
Tronsmo, A., Phytopathology 79(10):1153 (1989).
Sandhu, D. K., et al., Enzyme Microb. Technol, Jan. 1989, vol. 11, pp. 21–25.
Usui, T., et al., Carbohydrate Research, vol. 203, pp. 65—77 (1990).
De Vries, O. M. H., et al., J. Gen Microbiol. vol. 76, pp. 319–330 (1973).
Takara Biomedicals Brochure for Chitinase T–1 from Trichoderma, dated Apr. 1989.
Takara Biomedicals Brochure for β–N–Acetylhexosaminidase from *Trichoderma harzianum* AF6–T8, dated Apr. 1989.
Tronsmo, A., Biological Control vol. 1: 59–62 (Aug. 1991).
Lorito, M., et al., Phytopathology, vol. 82, No. 2, 245–246, (Feb. 1992).
Harman, G. E., et al., Proceedings of EFPP/IOBC Workshop, Copenhagen, Denmark, Jul. 1991.
DeLa Cruz, J., et al., Eur. J. Biochem. 206, 859–867 (1992).
Klemsdal, S. S., et al., 11th Nordic Postgraduate School in Plant Pathology, abstract of poster presented Feb. 3, 1992 in Tisvildeleije, Denmark.
Davies, D. A. L., et al., Nature, vol. 273, 18 May 1978, pp. 235–236.
Poulose, A. J., in Koeller, W., ed., *Target Sites of Fungicide Action*, CRC Press, Boca Raton, Fla., 1992, at pp. 313, 314, 317.
Roberts, D. P., et al., Phytopathology, vol. 80, No. 5, 461–465 (1990).
*Microbial Polysaccharides and Polysaccharases*, Berkeley, R. C. W., et al. eds., Academic Press, 1979, pp. 285–311 & 436–447.
Kitamoto, Y., et al., Agric. Biol. Chem. 51(12), 3385–3386, 1987.
Mauch, F., et al., Plant Physiol. vol. 88, 936–942 (1988).
Ridout, C. J., et al., Journal of General Microbiology, vol. 132, 2345–2352 (1986).
Tangarone, B., et al., Applied and Environmental Microbiology, vol. 55, 177–184 (Jan. 1989).
Ulhoa, C. J., et al., Current Microbiology, vol. 23, 285–289 (1991).
Ulhoa, C. J., et al., Journal of General Microbiology, vol. 137, 2163–2169 (1991).
*Methods in Enzymology*, vol. 161, Wood, W. A., et al., eds., 1988, Academic Press, pp. 479–484, 498–501.
Yabuki, M., et al., J. Gen. Appl. Microbiol., vol. 32, 25–38 (1986).
Harman, G. E., et al., Phytopathology, vol. 83, No. 3, 313–318 (1993).
DiPietro, A., et al., Phytopathology, vol. 83, No. 3, 308–313 (1993).
Lorito, M., et al., Phytopathology, vol. 83, No. 3, 302–307 (1993).
Ohtakara, A., et al., Chemical Abstracts 95: 75979w (Aug. 1981).
Otakara, A., Agr. Biol. Chem., vol. 27, No. 6, 454–460 (1963).
Yabuki, M., Derwent Biotechnology Abstracts, vol. 4, No. 15, Abstract 85–07729 (1985).
Yabuki, M., Derwent Biotechnology Abstracts, vol. 4, No. 15, Abstract 85–07730 (1985).
Roberts, W. K., et al., J. Gen. Microbiol 134: 169–176 (1988).
Van Hoof, A., et al., Physiological and Molecular Plant Pathology 39: 259–267 (1991).
Daugrois, J. H., et al., Arch. Biochem. Biophys. 292: 468–474 (1992).
Ulhoa, C. J., et al., Enz. Microb. Technol. 14: 236–240 (1992).
Mauch, F., et al. Plant Physiol. 87: 325–333 (1988).
Sullivan, P., et al., J. Gen. Microbiol. 130: 2213–2218 (1984).

*Primary Examiner*—David M. Naff
*Assistant Examiner*—Maria L. Osoteo

[57] ABSTRACT

N-acetyl-β-glucosaminidase isolated from *Trichoderma harzianum* strain P1 having accession No. ATCC 74058 has molecular mass of 72 kDa and isoelectric point of 4.6. Glucan 1,3-β-glucosidase isolated from *Trichoderma harzianum* strain P1 has molecular mass of 78 kDa and isoelectric point of 6.2. Combinations of endochitinase, chitin 1,4-β-chitobiosidase, N-acetyl-β-glucosaminidase and glucan 1,3-β-glucosidase have synergistic antifungal effect.

1 Claim, 12 Drawing Sheets

5,474,926

N-ACETYL-β-GLUCOSAMINIDASE ISOLATED FROM *TRICHODERMA HARZIANUM*

This invention was made at least in part with Government support under U.S.-Israel Binational Agricultural Research and Development Fund (BARD) grant number US-1723-89. The Government has certain rights in the invention.

CROSS-REFERENCE TO RELATED APPLICATION

This is a continuation-in-part of U.S. Ser. No. 07/990,609, filed Dec. 15, 1992, now U.S. Pat. No. 5,326,561.

TECHNICAL FIELD

This invention is directed at isolation of fungal cell wall degrading enzymes and to synergistic combinations of fungal cell wall degrading enzymes, for biological control of chitin- and β-1,3-glucan-containing fungi.

BACKGROUND OF THE INVENTION

Application of broad-spectrum pesticides is the primary method used for controlling fungal pests. Such application has resulted in significant environmental pollution and ecological disruption. Pesticide residues are found in food and groundwater and often eliminate beneficial organisms resulting in emergence of secondary pests. Furthermore, as the target pests become less susceptible to the pesticide, there can be a resurgence of the original pest, requiring application of excessive quantities of pesticides for control. This has resulted in a search for environmentally safer methods including biological control involving targeting an attribute that is pest specific and the use of synergistic combinations of fungicides to reduce the amounts of application.

One target that has been selected is the structural polymer chitin which is present in insects and some fungi that attack plants, but is absent in higher plants and vertebrates.

Suslow et al U.S. Pat. No. 4,751,681 contains claims directed to preparing bacteria for producing chitinase for the purpose of inhibiting plant pathogens.

Suslow et al U.S. Pat. No. 4,940,840 contains claims directed to introducing a DNA sequence encoding for the production of chitinase into plants so they are pathogen-resistant.

Harman et al U.S. Pat. No. 5,173,419 teaches obtaining purified endochitinase and chitin 1,4-β-chitobiosidase (referred to therein as exochitinase) from *Trichoderma harzianum* strain P1 having accession No. 74058 and use of the endochitinase to inhibit the germination and subsequent growth of chitin-containing fungi.

Harman et al U.S. patent application Ser. No. 07/919,784 teaches obtaining purified endochitinase and chitin 1,4-β-chitobiosidase (referred to therein as chitobiase) from *Trichoderma harzianum* strain P1 having accession No. 74058 and use of these to inhibit germination or replication of chitin containing fungi and antifungal synergistic combinations of endochitinase and chitin 1,4-β-chitobiosidase (referred to therein as chitobiase).

Harman et al U.S. patent application Ser. No. 07/990,609 is directed to antifungal synergistic combinations of fungal cell wall degrading enzyme and non-enzymatic fungicide, and Harman et al U.S. patent application Ser. no. 08/012,945 is directed to antifungal synergistic combinations of purified cell wall degrading enzyme and antifungal bacteria. Both of these teach obtaining purified glucan 1,3-glucosidase from *Trichoderma harzianum* strain P1 having accession No. 74058 for the cell wall degrading enzyme.

SUMMARY OF THE INVENTION

It is an object of one embodiment of the invention herein to obtain a purified N-acetyl-β-glucosaminidase from *Trichoderma harzianum* strain P1 having accession No. ATCC 74058 for use per se or in synergistic combinations to inhibit chitin-containing fungi or for use in providing chitinase-producing bacteria or for use in isolating the gene coding for it for insertion into a genome of a plant needing protection from a chitin-containing pest.

It is an object of a second embodiment of the invention herein to obtain a purified glucan 1,3-β-glucosidase from *Trichoderma harzianum* strain P1 having accession No. ATCC 74058 for use per se or in synergistic combinations to inhibit β-1,3-glucan-containing fungi or for use in providing glucosidase-producing bacteria or for use in isolating the gene coding for it for insertion into a genome of a plant needing protection from a β-1,3-glucan-containing pest.

It is an object of other embodiments of the invention herein to provide novel compositions for inhibiting the replication, germination or growth of a chitin- and β-1,3-glucan-containing fungus, which consist essentially of novel antifungal synergistic combinations of purified fungal cell wall degrading enzymes, and to provide a method of inhibiting the germination, replication or growth of said fungus by use of said novel antifungal synergistic combinations.

We turn firstly to the purified N-acetyl-β-glucosaminidase of the first embodiment of the invention herein. In particular, it is an essentially pure chitin-containing-fungus-inhibiting protein having N-acetyl-β-glucosaminidase activity, which is isolated from *Trichoderma harzianum* strain P1 having accession No. ATCC 74058 and which has a molecular mass of 72 kDa (as determined by sodium dodecyl sulfate polyacrylamide gel electrophoresis after the protein was prepared under reducing conditions, from a regression based on the log of the molecular weight of standard proteins), and an isoelectric point of 4.6 (as determined by isoelectric focusing electrophoresis from a regression of distance versus isoelectric point of standard proteins).

We turn secondly to the purified glucan 1,3-β-glucosidase of the second embodiment of the invention herein. In particular, it is an essentially pure β-1,3-glucan-containing-fungus-inhibiting protein having glucan 1,3-β-glucosidase activity, which is isolated from *Trichoderma harzianum* strain P1 having accession No. ATCC 74058 and which has a molecular mass of 78 kDa (as determined by sodium dodecyl sulfate polyacrylamide gel electrophoresis after the protein was prepared under reducing conditions, from a regression based on the log of molecular weight of standard proteins), and an isoelectric point of 6.2 (as determined by isoelectric focusing electrophoresis from a regression of distance versus isoelectric point of standard proteins).

We turn now to the embodiments of the invention directed to compositions for inhibiting the replication, germination or growth of a chitin- and β-1,3-glucan-containing fungus which consist essentially of novel antifungal synergistic combinations of purified fungal cell wall degrading enzymes.

One of these compositions consists essentially of essentially pure endochitinase and essentially pure N-acetyl-β- glucosaminidase in a weight ratio ranging from 3:1 to 1:3, preferably in a weight ratio of 1:1.

Another of these compositions consists essentially of essentially pure chitin 1,4-β-chitobiosidase and essentially pure N-acetyl-β-glucosaminidase in a weight ratio ranging from 3:1 to 1:3, preferably in a weight ratio of 1:1.

Another of these compositions consists essentially of essentially pure chitin 1,4-β-chitobiosidase and essentially pure glucan 1,3-β-glucosidase in a weight ratio ranging from 3:1 to 1:3, preferably in a weight ratio of 1:1.

Another of these compositions consists essentially of essentially pure N-acetyl-β-glucosaminidase and essentially pure glucan 1,3-β-glucosidase in a weight ratio ranging from 3:1 to 1:3, preferably in a weight ratio of 1:1.

Still another of these compositions consists essentially of (a) essentially pure endochitinase, (b) essentially pure chitin 1,4-chitobiosidase, and (c) essentially pure N-acetyl-β-glucosaminidase, in a weight ratio of (a):(b):(c) wherein (a), (b) and (c) each range from 1 to 3, and the weight ratio of (a):(b):(c) preferably is 1:1:1.

Still another of these compositions consists essentially of (a) essentially pure endochitinase, (b) essentially pure 1,4-β-chitobiosidase and (c) essentially pure glucan 1,3-β-glucosidase, in a weight ratio of (a): (b): (c) wherein (a) , (b) and (c) each range from 1 to 3, and the weight ratio of (a):(b):(c) preferably is 1:1:1.

Yet another of these compositions consists essentially of (a) essentially pure chitin 1,4-β-chitobiosidase, (b) essentially pure N-acetyl-β-glucosaminidase and (c) essentially pure glucan 1,3-β-glucosidase, in a weight ratio of (a):(b):(c) wherein (a), (b) and (c) each range from 1 to 3, and the weight ratio of (a):(b):(c) preferably is 1:1:1.

Yet another of these compositions consists essentially of (a) essentially pure endochitinase, (b) essentially pure chitin 1,4-β-chitobiosidase, (c) essentially pure N-acetyl-β-glucosaminidase and (d) essentially pure glucan 1,3-β-glucosidase, in a weight ratio of (a):(b):(c):(d) wherein (a), (b), (c) and (d) each range from 1 to 3, and the weight ratio of (a):(b):(c):(d) preferably is 1:1:1:1.

In the case of the above compositions, the preferred endochitinase, chitin 1,4-β-chitobiosidase, N-acetyl-β-glucosaminidase and glucan 1,3-β-glucosidase are each isolated from *Trichoderma harzianum* strain P1 having accession No. ATCC 74058.

A particular combination of endochitinase and glucan 1,3-β-glucosidase is known from Mauch, F., et al, Plant Physiol. 88,936–942 (1988) wherein these are denoted as chitinase and as β-1,3-glucanase. Novel composition herein consists essentially of essentially pure endochitinase and essentially pure glucan 1,3-β-glucosidase in a weight ratio ranging from 3:1 to 1:1, preferably in a weight ratio of 1:1, wherein the endochitinase and the glucan 1,3-β-glucosidase are each isolated from *Trichoderma harzianum* strain P1 having accession No. ATCC 74058.

We turn now to the methods herein of inhibiting the germination, replication or growth of a chitin and β-1,3-glucan containing fungus. These comprise contacting said fungus or the locus to be protected from said fungus, with an antifungal effective amount of any of the aforementioned compositions of the invention herein.

Where the molecular mass was determined by sodium dodecyl sulfate polyacrylamide gel electrophoresis after the protein was prepared under reducing condition, from regression based on the log of the molecular weight of standard proteins, the proteins used for determining molecular mass of the N-acetyl-β-glucosaminidase were 6 standard proteins obtained from Pharmacia LKB Biotechnology, having molecular weights ranging from 14.4 to 97.4 kDa, and the proteins used for determining molecular mass of the glucan 1,3-β-glucosidase were seven standard proteins obtained from Sigma Chemical Co., having molecular weights ranging from 14.2 to 66 kDa, and molecular weights were estimated from a regression equation of the log of molecular weight of the standard proteins versus distance migrated. The six standard proteins from Pharmacia LKB Biotechnology and their molecular weights in kDa are respectively α-lactalbumin, 14.4; trypsin inhibitor, 20.1; carbonic anhydrase, 30; ovalbumin 43; albumin, 67; and phosphorylase G, 94. The seven standard proteins from Sigma Chemical Co. and their molecular weights in kDa are respectively α-lactalbumin, 14.2; soybean trypsin inhibitor, 20.1; trypsinogen, phenylmethylsulfonyl fluoride treated, 24; carbonic anhydrase, 29; glyceraldehyde-3-phosphate, 36; egg albumin, 45; and bovine albumin, 66. When the isoelectric point was determined by isoelectric focusing electrophoresis from a regression of distance versus isoelectric point of standard proteins, comparison was to 12 standard proteins obtained from Pharmacia LKB Biotechnology having isoelectric points ranging from pH 3.5 to pH 9.3; the standard proteins and their isoelectric points are respectively amyloglucosidase, 3.5; methyl red dye, 3.75; soybean trypsin inhibitor, 4.55; β-lactoglobulin, 5.2; bovine carbonic anhydrase B, 5.85; human carbonic anhydrase B, 6.55; horse myoglobin cynocytic band, 6.85; horse myoglobin basic band, 7.35; lentil lectin acidic band, 8.15; lentil lectin middle band, 8.45; lentil lectin basic band, 8.65; and trypsinogen, 9.3. In both cases a linear regression was employed and $r^2$ values ranged from 0.94 to 0.99.

The term "essentially pure" is used herein to mean purified to be free of contaminating protein, i.e., a single protein band or a plurality of closely spaced protein bands representing different levels of N-glycosylation of the same protein, on a sodium dodecyl sulfate polyacrylamide gel submitted to electrophoresis under reducing conditions and stained with silver stain. When a composition is described as consisting essentially of essentially pure endochitinase, and/ or essentially pure chitin 1,4-β-chitobiosidase and/or essentially pure N-acetyl-β-glucosaminidase and/or essentially pure glucan 1,3-β-glucosidase, it is meant that the endochitinase, chitin 1,4-β-chitobiosidase, N-acetyl-β-chitobiosidase, glucan 1,3-β-glucosidase were purified to be free of contaminating protein for use as an ingredient in the composition.

The term "endochitinase" is used herein to refer to enzymes that randomly cleave chitin and have endochitinase activity. Endochitinase activity is readily measured by determining optical density at 510 nm as reduction of turbidity of a 1% suspension of moist purified colloidal chitin in 100 mM sodium acetate buffer, pH 5.5, or in 50 mMKHPO$_4$ buffer, pH 6.7, after 24 hours of incubation at 30° C. For calculation of specific activity, one unit is defined as the amount of enzyme required to obtain a 5% turbidity reduction.

The term "chitin 1,4-chitobiosidase" is used herein to refer to enzymes that cleave dimeric units from chitin from one end and have chitin 1,4-β-chitobiosidase activity. Chitin 1,4-β-chitobiosidases are sometimes referred to for convenience herein as chitobiosidases. Chitin 1,4-β-chitobiosidase activity is readily determined by measuring the release of p-nitrophenol from p-nitrophenyl-β -D-N,N'-diacetylchitobiose, e.g., by the following procedure. A substrate solution is formed by dissolving 3 mg of substrate in 10 ml 50 mM KHPO₄ buffer, pH 6.7. Fifty μl of substrate solution is added to a well in a microtiter plate (Corning). Thirty μl of test solution is added, and incubation is carried out at 50° C. for 15 minutes. Then the reaction is stopped by the addition of 50 μl of 0.4M $Na_4CO_3$, and the optical density is read at 410 nm. An activity of one nanokatal (nkatal) corresponds to the release of 1 nmol nitrophenol per second.

The term "N-acetyl-β-glucosaminidase" is used herein to refer to enzymes that cleave monomeric units from chitin from one end and have N-acetyl-β-glucosaminidase activity. N-acetyl-β-glucosaminidases may additionally have chitin 1,4-β-chitobiosidase activity, e.g., at a much lower specific activity which is first detectable at a time later than when N-acetyl-β-glucosaminidase activity is first detectable. N-acetyl-β-glucosaminidases may be referred to herein for convenience as glucosaminidases or as NAGases. N-acetyl-β-glucosaminidase activity is readily determined by measuring the release of p-nitrophenol from p-nitrophenyl-β-D-N-acetylglucosaminide, e.g., by the same procedure as described above for assaying for chitobiosidase activity except for the substitution of substrate. An activity of one nanokatal (nkatal) corresponds to the release of 1 nmol nitrophenol per second.

The term "glucan 1,3-β-glucosidase" is used herein to refer to enzymes that cleave 1,3-β-glucans and have glucan 1,3-β-glucosidase activity. Glucan 1,3-β-glucosidases may be referred to herein for conveniences as glucosidases. Glucan 1,3-β-glucosidase activity is readily determined by measuring the amount of reducing sugar release from laminarin in a standard assay containing 250 μl of enzyme solution and 250 μl of a 0.1% solution of laminarin in 50 mM potassium phosphate buffer, pH 6.7, wherein incubation is carried out at 30° C. for 1 hour whereupon 250 μl of a copper reagent (prepared by dissolving 28 g $Na_2PO_4$ and 40 g potassium sodium tartrate in 700 ml deionized water, adding 100 ml of 1N NaOH, then adding 80 ml of a 10% (W/V) solution of $CuSO_4.5H_2O$ with stirring, then adding 180 g $Na_2SO_4$, when all the ingredients have dissolved, bringing to 1 L with deionized water, then allowing to stand for 2 days, then decanting and filtering) is added, and the admixture is covered with foil and heated for 20 minutes in a steam bath, whereupon, after cooling, 250 μl of arsenomolybdate reagent (prepared by dissolving 25 g of $(NH_4)_6Mo_7O_{24}.4H_2O$ in 450 ml deionized water, adding 21 ml concentrated $H_2SO_4$ with mixing, then adding a solution containing 3 g $Na_2HAsO_4.7H_2O$ in 25 ml distilled water and mixing, incubating at 37° C. for 2 days and storing in a brown bottle until used) is added with mixing, followed by adding of 5 ml deionized water, and reading color in a spectrophotometer at 510 nm, and wherein appropriate controls without either enzyme or substrate are run simultaneously; the quantity of reducing sugar is calculated from glucose standards (1, 5, 10, 15, 30, 50 μg) included in the assay. An activity of one nkatal corresponds to the release of 1 nmol glucose equivalent per second under the above conditions.

The term "fungal cell wall degrading enzyme" is used herein to mean enzyme that effects lysis of fungal cell walls and refers to endochitinases, chitin 1,4-chitobiosidases, N-acetyl-β-glucosaminidases and glucan 1,3-β-glucosidases.

The term "inhibit" is used herein to mean reduce the growth and/or development of fungi compared to where inhibiting agent is not present.

The term "locus to be protected from such fungus" includes seeds, roots, stems, leaves, flowers and fruits to be protected and to the soil surrounding seeds and roots to be protected, as well as animal or human tissues or organs to be protected.

BRIEF DESCRIPTION OF THE DRAWINGS

FIG. 9 depicts graphs of percent inhibition versus total enzyme concentration where the enzyme is the endochitinase isolated from *Trichoderma harzianum* strain P1 having accession No. 74058.

FIG. 10 depicts graphs of percent inhibition versus total enzyme concentration where the enzyme is the chitobiosidase isolated from *Trichoderma harzianum* strain P1 having accession No. 74058.

FIG. 11 depicts graphs of percent inhibition versus total enzyme concentration where the enzyme is the NAGase isolated from *Trichoderma harzianum* strain P1 having accession No. 74058.

FIG. 12 depicts graphs of percent inhibition versus total enzyme concentration where the enzyme is the glucosidase isolated from *Trichoderma harzianum* strain P1 having accession No. 74058.

FIG. 13 depicts graphs of percent inhibition versus total enzyme concentration where the enzyme is the binary combination of the endochitinase and the chitobiosidase.

FIG. 14 depicts graphs of percent inhibition versus total enzyme concentration where the enzyme is the binary combination of the endochitinase and the NAGase.

FIG. 15 depicts graphs of percent inhibition versus total enzyme concentration where the enzyme is the binary combination of the endochitinase and the glucosidase.

FIG. 16 depicts graphs of percent inhibition versus total enzyme concentration where the enzyme is the binary combination of the chitobiosidase and the NAGase.

FIG. 17 depicts graphs of percent inhibition versus total enzyme concentration where the enzyme is the binary combination of the chitobiosidase and the glucosidase.

FIG. 18 depicts graphs of percent inhibition versus total enzyme concentration where the enzyme is the binary combination of the NAGase and the glucosidase.

FIG. 19 depicts graphs of percent inhibition versus total enzyme concentration where the enzyme is the ternary combination of the endochitinase and the chitobiosidase and the NAGase.

FIG. 20 depicts graphs of percent inhibition versus total enzyme concentration where the enzyme is the ternary combination of the endochitinase and the chitobiosidase and the glucosidase.

FIG. 21 depicts graphs of percent inhibition versus total enzyme concentration where the enzyme is the ternary combination of the endochitinase and the NAGase and the glucosidase.

FIG. 22 depicts graphs of percent inhibition versus total enzyme concentration where the enzyme is the ternary combination of the chitobiosidase and the NAGase and the glucosidase.

FIG. 23 depicts graphs of percent inhibition versus total enzyme concentration where the enzyme is the quaternary combination of the endochitinase and the chitobiosidase and the NAGase and the glucosidase.

DETAILED DESCRIPTION

Figure 1:
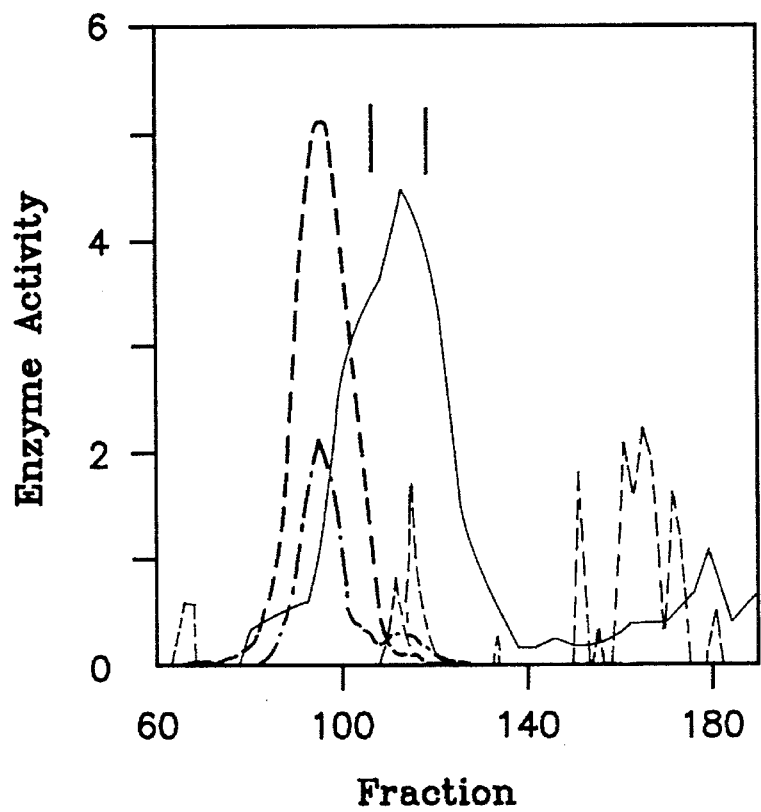
FIG. 1 depicts the elution pattern obtained on gel filtration chromatography in Example I and provides graphs of enzyme activity vs. fraction.

*Trichoderma harzianum* strain P1 arose as a spontaneously occurring isolate on placement of *Trichoderma harzianum* strain 107 on a medium containing 500 ppm of the fungicide iprodione by inventor A. Tronsmo. Strain P1 was deposited with the American Type Culture Collection, 12301 Parklawn Drive, Rockville, Md. 20852 on May 20, 1991, under the terms of the Budapest Treaty, and has been assigned accession No. ATCC 74058. Strain 107 was isolated from wood shavings by Dr. C. Dennis in Norfolk, England and was selected by Tronsmo and Dennis as a cold tolerant isolate in a survey for biocontrol agents effective in cold climates. *Trichoderma harzianum* strain P1 (ATCC 74058) has been evaluated as a biocontrol agent as described in Tronsmo, A., *Norwegian Journal of Agricultural Sciences*, 3, 157–161, 1989 (biological control of storage rot on carrots) and has been successfully used as a biocontrol agent of Botrytis cinerea, a fungus affecting strawberries, grapes and applies as described in Tronsmo, A., Biological Control, 1, 59–62, 1991 and Harman, G. and Tronsmo, A., unpublished.

We turn now to the aforedescribed essentially pure chitin-containing-fungus-inhibiting protein having N-acetyl-β-glucosaminidase activity, which is isolated from *Trichoderma harzianum* strain P1 having accession No. ATCC 74058. It is readily obtained and purified by culturing *Trichoderma harzianum* strain P1 in RM medium and purifying to homogeneity by column gel filtration, chromatofocusing and isoelectric focusing, as described in detail in Example I hereinafter. It has good activity over a pH range of 4 to 7 and optimal activity between pH 5.0 and 5.5, as determined in a 50 mM citric acid/potassium phosphate buffer mixture at pH levels ranging from 3.0 to 9.0. It has good activity over a temperature range of 25° to 85° C. with optimal activity at 60° to 70° C., as determined in 50 mM potassium phosphate buffer pH 6.7 at temperatures between 20° C. and 100° C. It is quite resistant to heat inactivation, retaining about 70, 25 and 10% of activity after 15 minutes at 80°, 90° and 100° C., respectively. In Example I hereinafter, it is purified to an N-acetyl-β-glucosaminidase specific activity 9-fold that of its activity in the crude culture filtrate. It was reproducibly calculated to have an N-acetyl-β-glucosaminidase specific activity of about 12 nkatal/mg under the assay conditions for this activity set forth above. The purified protein also showed a low level of chitin 1,4-chitobiosidase activity and particularly was reproducibly calculated to have a chitin 1,4-chitobiosidase specific activity of 1.5 nkatal/mg under the assay conditions for this activity set forth above; this activity was first detectable at a time later than when the N-acetyl-β-glucosaminidase activity was first detectable. It inhibits spore germination and hyphal elongation of Botrytis cinerea and is synergistic with other cell wall degrading enzymes as demonstrated hereinafter.

We turn now to the aforedescribed essentially pure β-1,3-glucan-containing-fungus-inhibiting protein having glucan 1,3-β-glucosidase activity, which is isolated from *Trichoderma harzianum* strain P1 having accession No. ATCC 74058. It is readily obtained and purified by culturing *Trichoderma harzianum* strain P1 having accession No. ATCC 74058 in SMCS medium and purifying to homogeneity by column gel filtration and chromatofocusing as described in detail in Example II hereinafter. The fact that it is produced in the absence of laminarin indicates that β-1,3-glucan is not required for its induction. It has good activity over a pH range of 4.0 to 7.5, with optimal activity between pH 4.5 and 5.5, as determined in a 50 mM citric acid/potassium phosphate buffer mixture at pH levels ranging from 3.0 to 9.0 It has good activity over a temperature range of 25° to 55° C. with optimal activity at 40° to 45° C. and negligible activity starting at 60° C., as determined in 50 mM potassium phosphate buffer pH 6.7 at temperatures between 20° C. and 100° C. It cleaved laminarin under the assay conditions for glucan 1,3-β-glucosidase activity set forth above. In Example II hereinafter, it is purified to a glucan 1,3-β-glucosidase specific activity 36-fold that of its activity in a dialyzed culture filtrate and was reproducibly calculated to have a glucan 1,3-β-glucosidase specific activity of about 150 nkatal/mg under the assay conditions for this activity set forth above. It did not release p-nitrophenol from P-nitrophenyl-β-glucopyranoside in assays wherein 50 μl enzyme solution and 50 μl of a 0.03% w/v p-nitrophenyl-β-glucopyranoside solution in 50 mM potassium buffer pH 6.7 were mixed in a microtiter plate well and incubated at 37° C. for 1, 6 and 24 hours and optical density is read at 405 nm to determine p-nitrophenol release. The amino acid composition of the enzyme was determined to be: aspartic acid plus asparagine, 14%; glutamic acid plus glutamine, 7.4%; serine, 9%; glycine, 11.7%; histidine, 1.2%; arginine, 2.5%; threonine, 8.6%; alanine, 8.7%; proline, 4%, tyrosine, 5.6%; valine, 6.9%; methionine, 1.3%, cysteine, 0.8%; isoleucine, 6.4%; leucine, 5.2%, phenylalanine, 4.2%; and lysine, 3%.

We turn now to the embodiments of the invention directed to compositions for inhibiting the replication, germination or growth of a chitin- and β-1,3-glucan-containing-fungus, which consist essentially of novel antifungal synergistic combinations of purified fungal cell wall degrading enzymes, i.e., purified endochitinases, chitin 1,4-β-chitobiosidases, N-acetyl-β-glucosaminidases and glucan 1,3-β-glucosidases.

The purified cell wall degrading enzymes for the synergistic combinations herein can be obtained from fungi, e.g., from the genera Trichoderma, Gliocladium, Lycoperdon and Calvatia; from bacteria, e.g., from the genera Streptomyces, Vibrio, Serratia and Bacillus; and from higher plants, e.g., Nicotiana, Cucumis and phaesolus.

Essentially pure fungal cell wall degrading enzymes are obtained from source microorganisms by culturing the source microorganism, concentrating the culture filtrate, fractionating by gel filtration chromatography, concentrating and further purifying by chromatofocusing and concentrating, followed if necessary, by fractionating by isoelectrofocusing in a Rotofor cell (BioRad, Richmond, Calif.) and concentrating. Essentially pure fungal cell wall degrading enzymes are obtained from source plants by procedures usually employed in protein purification. These include extraction of enzymes from plant tissues containing these proteins, precipitation of protein mixtures by addition of ammonium sulfate followed by dialysis, and then chromatography via ion exchange, gel permeation, or affinity or combinations of these, to obtain purified enzymes. Isoelectric focusing may also be used. An example of purification of a chitinase from bean leaves is set forth in Boller, T , et al, "Chitinase from Phaseolus vulgaris Leaves" in Wood, W. A., et al, Methods of Enzymology, Vol. 161, Academic Press, 1988, pages 479–484. An example of purification of an endochitinase from wheat is set forth in Cabib, E., "Endochitinase from Wheat Germ" in Wood, W. A., et al, Methods of Enzymology, Vol. 161, Academic Press, 1988, pages 498–501.

The sources for the enzymes are preferably microorganisms from the genera Trichoderma and Gliocladium. Species of Trichoderma include, for example, harzianum, reesei, longibrachiatum, konongii, viride, hamatum and aureoviride. Species of Gliocladium include, for example, virens, catenulatum and roseum.

The preferred source for endochitinase, chitin 1,4-β-chitobiosidase, N-acetyl-β-glucosaminidase and glucan 1,3-β-glucosidase enzymes herein is *Trichoderma harzianum* strain P1 having accession No. 74058.

Endochitinase from *Trichoderma harzianum* strain P1 having accession No. 74058 has a molecular mass of 36 kDa (as determined by sodium dodecyl sulfate polyacrylamide gel electrophoresis after the protein was prepared under reducing conditions, on direct comparison to migration of a 36 kDa protein) and an isoelectric point of 5.3±0.2 as determined based on its elution profile from a chromatofocusing column, and a molecular weight of 40 kDa (as determined by sodium dodecyl sulfate polyacrylamide gel electrophoresis after the protein was prepared under reducing conditions, from a regression based on the log of molecular weight of standard proteins) and an isoelectric point of 3.9 as determined by isoelectric focusing electrophoresis from a regression of distance versus the isoelectric point of standard proteins. The specific activity of the purified endochitinase was determined to be 0.86 units/µg protein with the turbidity reducing assay and 2.2 nkatal/µg protein when nitrophenyl-β-D-N,N'N"-triacetylchitotriose was used as a substrate. The production and purification to homogeneity of this endochitinase are described in Harman et al U.S. Pat. No. 5,173,419, and also in U.S. patent application Ser. No. 07/919,784, filed Jul. 27, 1992.

Chitin 1,3-β-chitobiosidase from *Trichoderma harzianum* strain P1 having accession No. 74058 in its most prevalent form has a molecular weight of 36 kDa (as determined by sodium dodecyl sulfate polyacrylamide gel electrophoresis after the protein was prepared under reducing conditions, on direct comparison to migration of a 36 kDa protein), and an isoelectric point of 4.4±0.2 as determined based on its elution profile from a chromatofocusing column, and a molecular weight of 40 kDa (as determined by sodium dodecyl sulfate polyacrylamide gel electrophoresis after the protein was prepared under reducing conditions, from a regression based on the log of the molecular weight of standard proteins), and an isoelectric point of 3.9 as determined by isoelectric focusing electrophoresis from a regression of distance versus isoelectric point of standard proteins. Conditions for molecular weight determination and isoelectric point determination are described in detail in U.S. patent application Ser. No. 07/919,784. It has an optimum pH for activity of about 3 to 7. The production and purification of this chitobiosidase are described in Harman et al U.S. Pat. No. 5,173,419 where it is referred to as a chitobiase, and also in U.S. patent application Ser. No. 07/919,784, filed Jul. 27, 1992, where it is referred to as a chitobiase and also as a chitobiosidase. The enzyme obtained in Ser. No. 07/919,784 has a specific activity of 127 nkatal/mg protein and is purified to greater than a 200-fold increase in specific activity compared to its activity in the culture filtrate. Ser. No. 07/919,784 refers to the presence also for a minor bind at 36 kDa. It has since been discovered that the chitobiosidase from *Trichoderma harzianum* strain P1 (ATCC 74058) gives three closely spaced protein bands with molecular weights of 40 kDa (staining most intensely), 38 kDa (faintest stain) and 35 kDa (intermediate intensity stain), as determined by sodium dodecyl sulfate polyacrylamide gel electrophoresis after the protein was prepared under reducing conditions, from a regression based on the log of the molecular weight of standard proteins, and that the three bands represent different levels of N-glycosylation of the same protein.

N-acetyl-β-glucosaminidase from *Trichoderma harzianum* strain P1 having accession No. 74058 is the N-acetyl-β-glucosaminidase described above having a molecular mass of 72 kDa and an isoelectric point of 4.6.

Glucan 1,3-β-glucosidase from *Trichoderma harzianum* strain P1 having accession No. 74058 is the glucan 1,3-β-glucosidase described above having a molecular mass of 78 kDa and an isoelectric point of 6.2.

A good source for endochitinase, chitin 1,4-β-chitobiosidase, N-acetyl-β-glucosaminidase and glucan 1,3-β-glucosidase is Gliocladium virens strain 41 having accession No. ATCC 20906. The endochitinase has a molecular weight of 41 kDa (as determined by sodium dodecyl sulfate polyacrylamide gel electrophoresis after the protein was prepared under reducing conditions, from a regression based on the log of the molecular weight of standard proteins), and an isoelectric point of 7.8 as determined by isoelectric focusing electrophoresis from a regression of distance versus isoelectric point of standard proteins. The procedures used for molecular weight determination and isoelectric point determination are the same as those described in detail hereinbefore. The enzyme is active in citric acid/$K_3(PO_4)$ buffer over a pH range of 3.5 to 7.0 and shows a 90–100% activity between pH 4.0 and 6.0 and shows maximum activity at pH 4.5. The optimum temperature for endochitinase activity at pH 5.5 is between 30 and 37° C., and activity drops off sharply at temperatures above 40° C. The production and purification to homogeneity of this enzyme are described in detail in Reference Example 1 in parent U.S. patent application Ser. No. 07/990,609. The enzyme was purified to an activity 105-fold that of its activity in the culture filtrate.

The synergistic enzyme combinations herein are suitable to provide the fungal cell wall degrading enzyme in the antifungal compositions comprising fungal cell wall degrading enzyme and non-enzymatic fungicide described in parent U.S. patent application Ser. No. 07/990,609, and in the antifungal compositions comprising fungal cell wall degrading enzymes and antifungal bacteria described in Harman et al U.S. patent application Ser. No. 08/012,945.

The essentially pure protein herein having N-acetyl-β-glucosaminidase activity which is isolated from *Trichoderma harzianum* strain P1 having accession No. 74058, the essentially pure protein herein having glucan 1,3-β-glucosidase activity which is isolated from *Trichoderma harzianum* strain P1 having accession No. 74058, and the novel antifungal synergistic combinations of purified fungal cell wall degrading enzymes are for application to fungi containing a structurally necessary amount of chitin and β-1,3-glucan, e.g., species from genera including Bipolaris, Botrytis, Collectotrichum, Diplodia, Fusarium, Gliocladium, Gymnosporangium, Rhizoctonia, Trichoderma, Uncinula, Ustilago, Venturia, Erysiphe, Saccharomyces, Sclerotium and Alternaria, and to loci to be protected from said fungi. Specific working examples herein show application to *Botrytis cinerea*, a fungus which is pathogenic to fruits including grapes, raspberries, apples, and to beans and other crops, and which was selected in the work supporting this invention as a model test fungus.

The purified N-acetyl-β-glucosaminidase herein and the purified glucan 1,3-β-glucosidase herein and the novel antifungal synergistic combinations of purified fungal cell wall degrading enzymes are used per se for antifungal utility or are readily formulated into antifungal compositions by admixing with non-toxic carriers appropriate for the particular use for a composition, e.g., agriculturally acceptable carriers for agricultural uses and pharmaceutically acceptable carriers for medicinal uses. They may be formulated as liquids (solutions or suspensions) and applied, e.g., as a spray, or as solids (e.g., with adhesive carriers, e.g., methyl cellulose or gum arabic) and applied as a powder. In liquids, the enzymes may be used, for example, at a concentration of 1 ppm to 1000 ppm enzyme.

For medicinal purposes (i.e., human and veterinary therapy) the enzymes or compositions herein can be administered in the same way as non-enzymatic fungicide is applied, e.g., topically applied to the skin of a human or non-human animal. Administration can also be, at least in some instances, via parenteral injection, e.g., intraperitoneally; this administration route is particularly useful where the immune system has been compromised since immune-deficient humans and individuals will inactivate enzymatic proteins more slowly than normal individuals. In addition, the enzymes or compositions herein can be added to solutions to be employed for medical or other purposes, to protect them from fungal contamination.

For agricultural purposes, application can be, for example, to the seeds, foliage, roots or fruit of a plant to be protected, or to the soil surrounding said plant, or to the fungus thereon which is to be inhibited. Normally, application is topical. However, other administration strategies can be used. For example, a gene coding for a fungal cell wall degrading enzyme can be isolated from microorganisms or other organisms producing it, and the gene inserted into the plant genome where it will produce the enzyme(s) inside the plant, or transgenic endophytic microorganisms producing fungal cell wall degrading enzyme(s) can be used to infect plants internally, typically in the xylem, to produce enzyme(s) internally in the plant, or transgenic plant-surface-colonizing microorganisms producing fungal cell wall degrading enzyme(s) can be used to protect the plants.

The multiple embodiments of the invention are illustrated by the following working examples.

Example I

Purified N-Acetyl-β-Glucosaminidase

Culturing was carried out in modified Richard's medium denoted RM medium above (containing in one liter of water, 10 g $KNO_3$, 5 g $KH_2PO_4$, 13 g $MgSO_4$, 20 mg $FeCl_3$, 10 g crab shell chitin (Sigma Chemicals), 10 g Polyclar AT (an insoluble polyvinylpyrrolidone from GAF Corp.) and 150 ml V8®vegetable juice (Campbell Soup Company)).

One hundred ml of the admixture was placed in a 250 ml Erlenmeyer flask.

The flask was inoculated with conidia grown by inoculation of potato dextrose agar (conidia of *Trichoderma harzianum* strain P1 having accession No. ATCC 74058) to provide $10^7$ conidia $ml^{-1}$ medium and the admixture was incubated at 25° C. for 5 days on a rotary shaker at 200 rpm. The culture filtrate was harvested by centrifugation at 8000×g for 10 minutes and removal of residual particulates by filtration through a glass fiber filter.

Purified N-acetyl-β-glucosaminidase was isolated from the culture filtrate as described below with all steps being carried out at 4° C. except for concentration which was carried out at room temperature.

Figure 2:
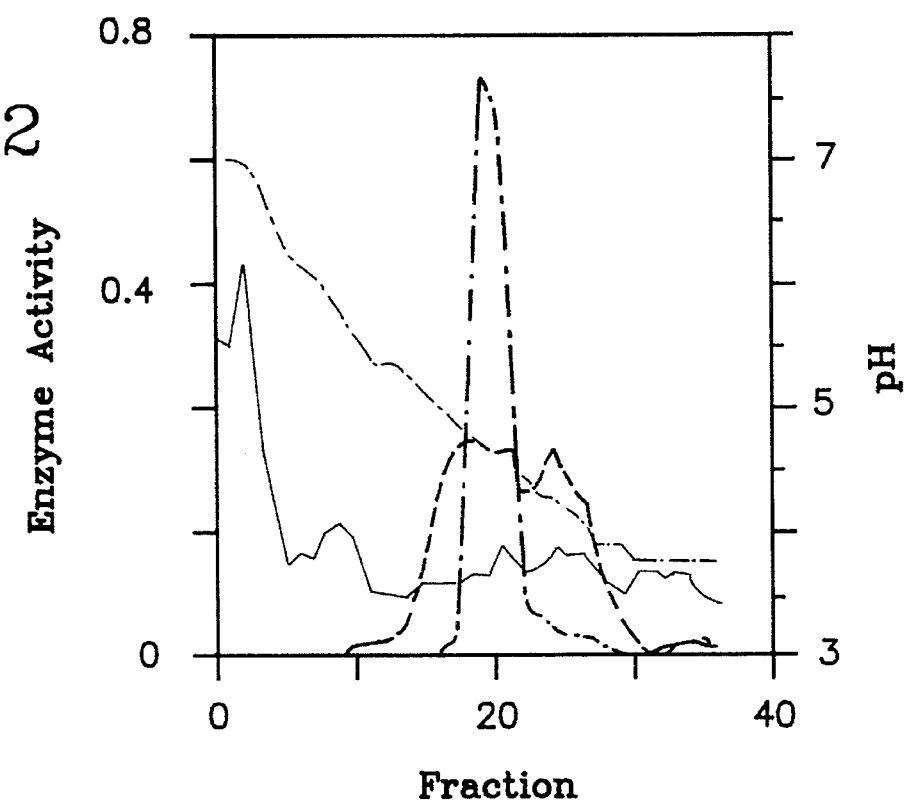
FIG. 2 depicts the elution pattern obtained in Example I on chromatofocusing separation of selected fractions obtained from gel filtration chromatography, and provides graphs of enzyme activity vs. fraction and pHvs. fraction.
Figure 3:
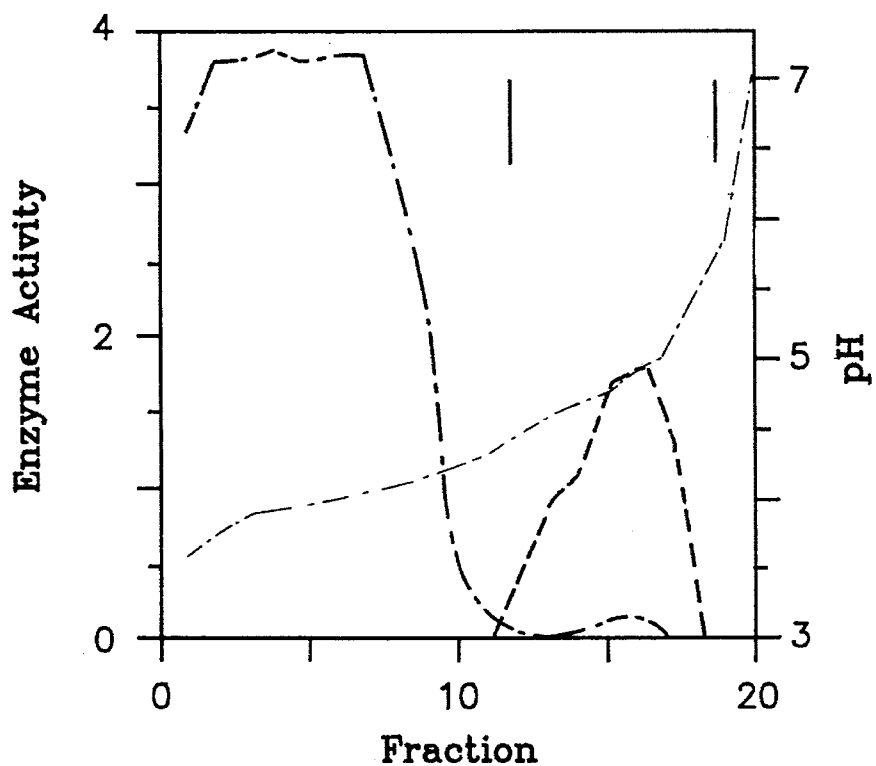
FIG. 3 depicts the elution pattern obtained in Example I for separation according to isoelectric point on a Rotofor apparatus of selected fractions from chromatofocusing separation, and provides graphs of enzyme activity vs. fraction and of pHvs. fraction.

The filtered culture filtrate was transferred into dialysis tubing (6,000 to 8,000 Da cutoff) and concentrated 30–40-fold by placing the tubing in solid polyethylene glycol (35,000 MW; Fluka Chemika-Biochemika, Buchs, Switzerland). The concentrate was dialyzed overnight against 50 mM potassium phosphate buffer pH 6.7 (5 L buffer $L^{-1}$ culture filtrate) and applied to a gel filtration column (5×60 cm) containing Sephacryl S-300 HR (Pharmacia LKB Biotechnology, Uppsala, Sweden) equilibrated with 50 mM potassium phosphate buffer pH 6.7 containing 200 mM NaCl. The material from 1 L of culture medium was chromatographed separately in two samples on Sephacryl S-300 HR. Fractions, approximately 8 ml each, were eluted with 1500 ml of 50 mM potassium phosphate buffer containing 200 mM NaCl. The elution pattern is shown in FIG. 1 wherein the continuous graph denotes glucosidase activity, the bold dashed line denotes NAGase activity, the other dashed line denotes endochitinase activity and the line made up of dots and dashes denotes chitobiosidase activity. Activity was not detected prior to fraction 60. The fractions of interest (between the vertical bars in FIG. 1) were pooled. The pooled fractions (120 ml) were transferred into dialysis tubing (6,000 to 8,000 Da cut-off) and concentrated by placing the tubing in solid polyethylene glycol (35,000 MW; Fluka Chemika-Biochemika, Buchs, Switzerland) and dialyzed overnight against a 20-fold volume of 25 mM imidazole/HCl buffer, pH7. The sample (about 20 ml) was then applied to a chromatofocusing column (1×30 cm) packed with PBE94 (Pharmacia LKB), and equilibrated with 25 mM imidazole/HCl buffer, pH 7. The column was eluted at a flow rate of 50 ml $h^{-1}$ with 320 ml composition consisting of Polybuffer 74 (Pharmacia LKB) diluted 1:8 with water, i.e., from pH 7 to 3.6, to provide fractions of approximately 8 ml. The elution pattern is shown in FIG. 2 wherein the continuous graph denotes glucosidase activity, the bold dashed line denotes NAGase activity, the bold line made up of dots and dashes denotes chitobiosidase activity and the other line made up of dots and dashes denotes pH. The fractions of interest (between the vertical bars of FIG. 2) were pooled. As indicated in FIG. 2., these contained NAGase and chitobiosidase activities. The pooled fractions (about 80 ml) were dialyzed first against a 20-fold volume of 1M NaCl and then against a 40-fold volume of distilled water to remove Polybuffer, and concentrated to a volume of 2 ml in a collodion bag system (10,000 Da cutoff; UH 100/1, Schleicher & Schuell Inc., Keene, N.H.). The concentrated sample was diluted to about 35 ml with deionized water and 2 ml Bio-LyteAmpholytes (Bio-Rad Laboratories, Richmond, Calif.) were added. Then the mixture was applied in approximately equal amounts to each of the compartments of a Rotofor Isoelectric Focusing apparatus (Bio-Rad) and separation was accomplished over about a 4 hour period. The fractions (each about 1.5 ml) were collected and assayed for enzyme activity. The elution pattern is shown in FIG. 3 wherein the bold dashed line denotes NAGase activity, the bold line made up of dots and dashes denotes chitobiosidase activity and the other line made up of dots and dashes denotes pH. The peak fractions as denoted by the vertical bars in FIG. 3 were pooled, dialyzed first against a 20-fold volume of 1M NaCl and then against a 40-fold volume of distilled water to remove Bio-LyteAmpholytes, and concentrated to a volume of 2 ml in a collodion bag system as described above.

The results of the purification are summarized in Table 1 below wherein the specific activity refers to specific activity against p-nitrophenyl-$\beta$-D-N-acetylglucosaminide.

TABLE 1

| Step | Total protein (mg) | Enzyme activity (nkatal) | Specific activity (nkatal mg$^{-1}$) | Purification (fold) | Yield (%) |
|---|---|---|---|---|---|
| Culture filtrate | 1850 | 2413.4 | 1.3 | 1.0 | 100 |
| Dialyzed Culture Filtrate | 850 | 2125.5 | 2.5 | 1.9 | 88 |
| Sephacryl S-300 HR | 17.6 | 74.3 | 4.2 | 3.2 | 3 |
| Chromatofocusing | 4.0 | 24.3 | 6.0 | 4.6 | 1 |
| Isoelectric focusing | 1.5 | 17.4 | 11.8 | 9.0 | 0.7 |

The concentrated peak fractions obtained as a result of the purification contained homogeneous N-acetyl-$\beta$-glucosaminidase as shown by the presence of a single protein band upon SDS-PAGE and upon Native PAGE in a PhastGel system (Pharmacia LKB). NAGase activity was visualized as fluorescent bands on polyacrylamide gels by use of 4-methylumbelliferyl-N-acetyl-$\beta$-glucosaminide as described by Tronsmo, A., and Harman, G. E., Anal. Biochem. 208: 74–79 (1993).

In addition to having activity on p-nitrophenyl-$\beta$-D-N-acetylglucosaminide, the purified N-acetyl-$\beta$-glucosaminidase was also active against p-nitrophenyl-$\beta$-D-N,N'-diacetylchitobiose, as shown in FIG. 3. The specific activity against p-nitrophenyl-$\beta$-D-N,N'-diacetylchitobiose of the purified N-acetyl-$\beta$-glucosaminidase (after isoelectric focusing) was determined to be 1.5 nkatal mg$^{-1}$.

Figure 4:
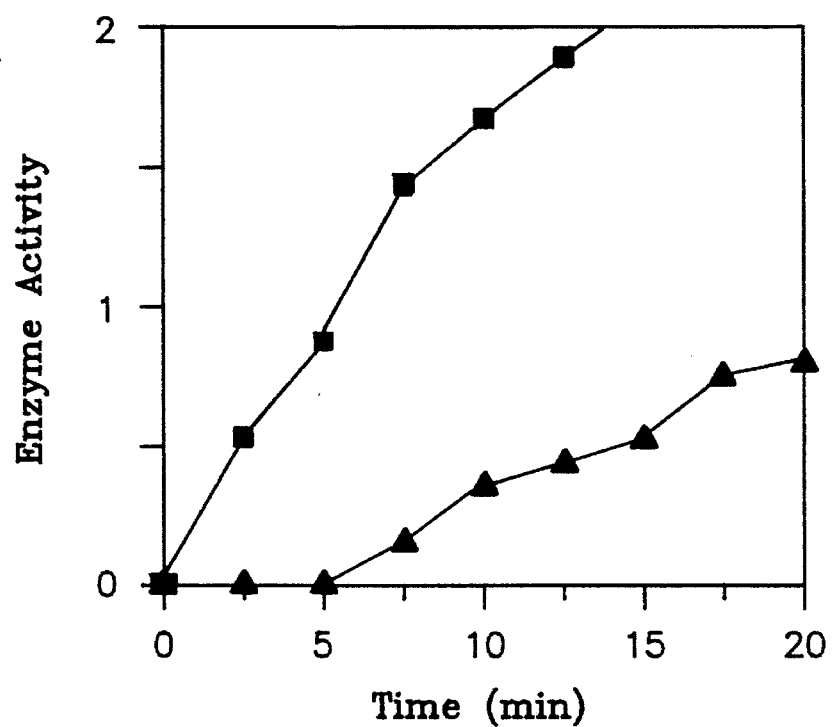
FIG. 4 depicts the time course of enzyme activity of the purified N-acetyl-β-glucosaminidase.

The specific activity against the monomeric substrate (p-nitrophenyl-$\beta$-D-N-acetylglucosaminide) was approximately 8-fold higher than the specific activity against the dimeric substrate (p-nitrophenyl-$\beta$-D-N,N'-diacetylchitobiose). The enzyme activity against the monomeric substrate was clearly detectable within 20 seconds of incubation, while 5 minutes was needed before any activity could be detected using the dimeric substrate. The time course of enzyme activity of the purified N-acetyl-$\beta$-glucosaminidase is shown in FIG. 4 wherein the squares denote activity against the monomeric substrate and the triangles denote activity against the dimeric substrate.

The purified enzyme showed no affinity for polyclonal antibodies prepared against purified glucanase, endochitinase or chitobiosidase from *Trichoderma harzianum* strain P1 having accession No. ATCC 74058.

The purified enzyme was determined (by sodium dodecyl sulfate polyacrylamide gel electrophoresis after the protein was prepared under reducing conditions, from a regression based on the log of molecular weight of standard proteins as described above) to have a molecular mass of 72 kDa and was determined (by isoelectric focusing electrophoreses from a regression of distance versus isoelectric point of standard proteins as described above) to have an isoelectric point of 4.6.

Figure 5:
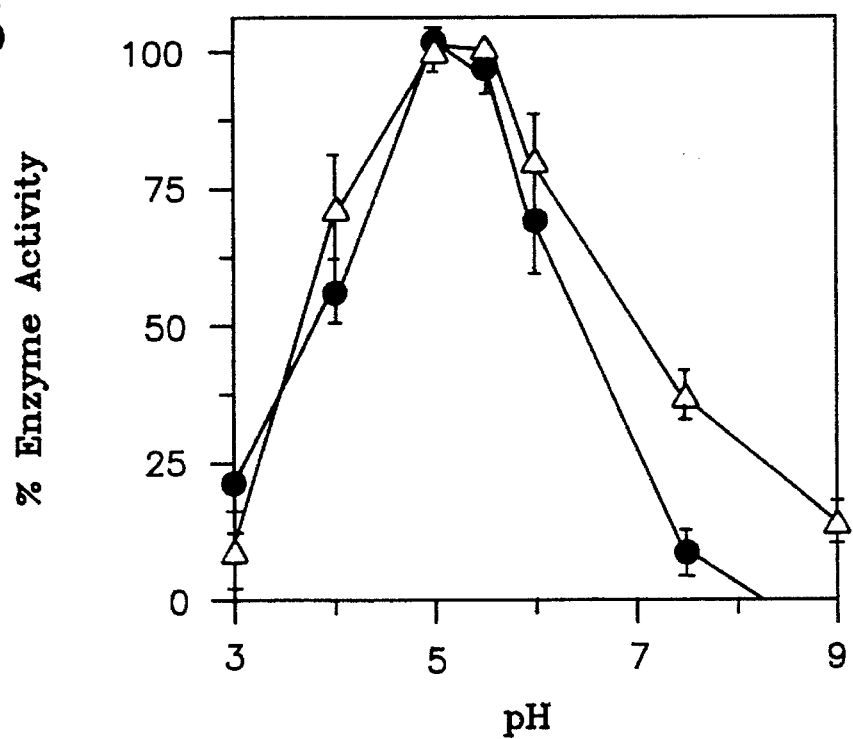
FIG. 5 depicts the effect of pH on the N-acetyl-β-glucosaminidase activity of the purified N-acetyl-β-glucosaminidase (graph denoted by circles) and on the glucan 1,3-β-glucosidase activity of the purified glucan 1,3-β-glucosidase (graph denoted by triangles).

The effect of pH on N-acetyl-$\beta$-glucosaminidase activity (determined as described above) for the purified enzyme is shown by the graph in FIG. 5 defined by circles.

Figure 6:
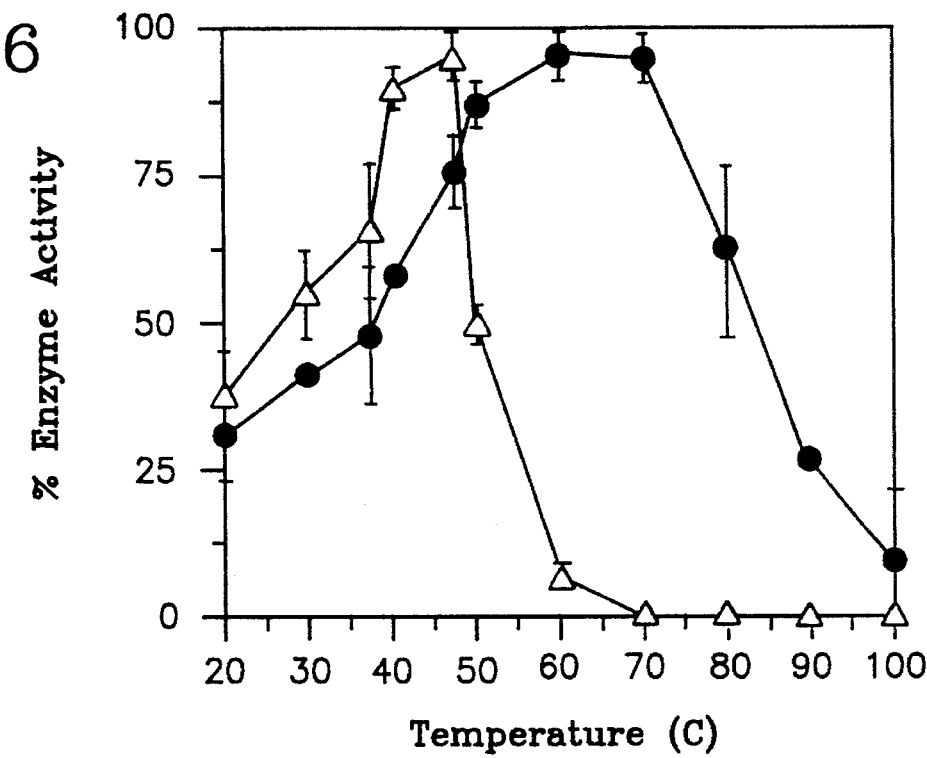
FIG. 6 depicts the effect of temperature on the N-acetyl-β-glucosaminidase activity of the purified N-acetyl-β-glucosaminidase (graph denoted by circles) and on the glucan 1,3-β-glucosidase activity at the purified glucan 1,3-β-glucosidase (graph denoted by triangles).

The effect of temperature on N-acetyl-$\beta$-glucosaminidase activity (determined as described above) for the purified enzyme is shown by the graph in FIG. 6 defined by circles.

Example II

Purified Glucan 1,3-$\beta$-Glucosidase

Synthetic medium denoted SMCS medium was made up containing 680 mg KHl PO$_4$, 870 mg K$_2$HPO$_4$, 200 mg KC$_1$, 1 g NH$_4$NO$_3$, 200 mg CaCl$_2$, 200 mg MgSO$_4$.7H$_2$O, 2 mg FeSO$_4$, 2 mg ZnSO$_4$, 2 mg MnSO$_4$, 42 g moist purified colloidal chitin (prepared as described in Vessey, J. C., et al, Trans. Br. Mycol. Soc. 60:710–713, 1973), 5 g sucrose, in 1 L distilled water, final pH 6.0.

100 ml of the synthetic medium as placed in a 250 ml Erlenmeyer flask.

The flask was inoculated with conidia grown by inoculation of potato dextrose agar (conidia of *Trichoderma harzianum* strain P1 having accession No. ATCC 74058) to provide 10$^7$ conidia ml$^{-1}$ medium and the admixture was incubated at 25° C. for 5 days on a rotary shaker at 200 rpm. The culture filtrate was harvested by centrifugation at 8000×g for 10 minutes and removal of residual particulates by filtration through a glass fiber filter.

Purified glucan 1,3-$\beta$-glucosidase was isolated from the culture filtrate as described below with all steps being carried out at 4° C. except for concentration which was carried out at room temperature.

Figure 7:
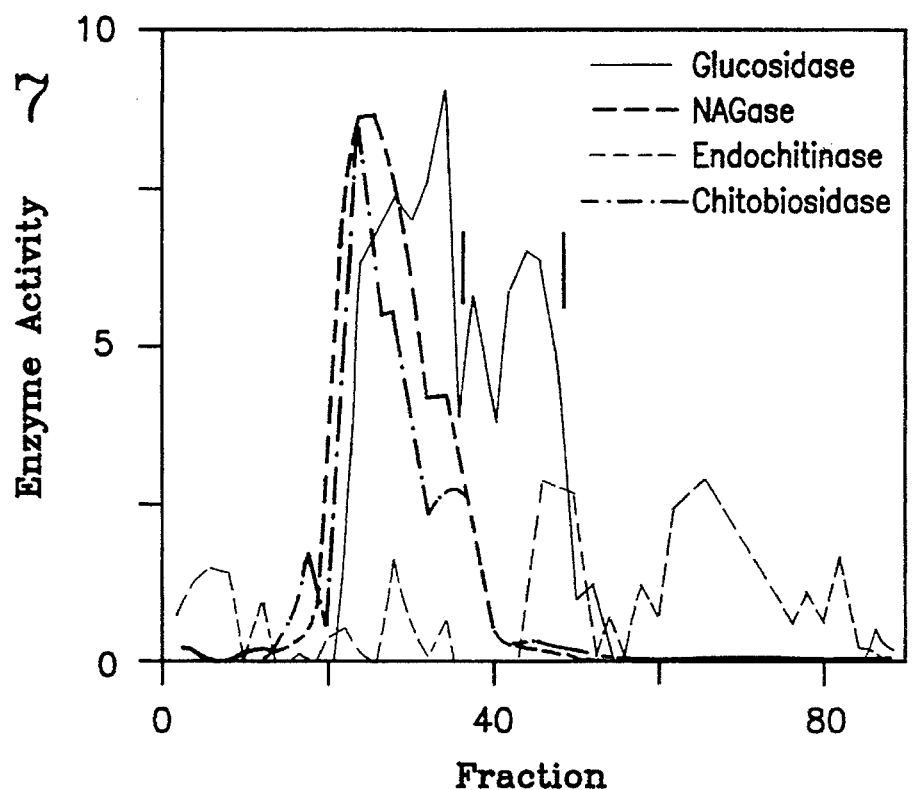
FIG. 7 depicts the elution pattern obtained on gel filtration chromatography in Example II and provides graphs of enzyme activity vs. fraction.
Figure 8:
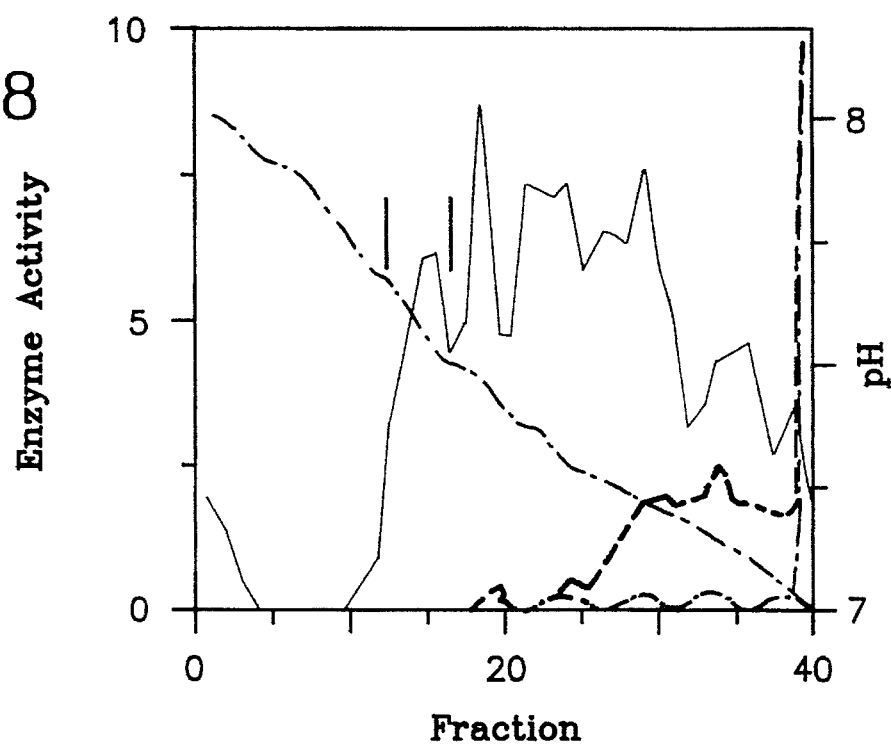
FIG. 8 depicts the elution pattern obtained in Example II on chromatofocusing separation of selected fractions obtained from gel filtration chromatography, and provides graphs of enzyme activity vs. fraction and pH vs. fraction.

The filtered culture filtrate was transferred into dialysis tubing (6,000 to 8,000 Da cutoff) and concentrated 30–40-fold by placing the tubing in solid polyethylene glycol (35,000 MW; Fluka Chemika-Biochemika, Buchs, Switzerland). The concentrate was dialyzed overnight against 50 mM potassium phosphate buffer pH 6.7 (5 L buffer L$^{-1}$ culture filtrate) and applied to a gel filtration column (5×60 cm) containing Sephacryl S-300 HR (Pharmacia LKB Biotechnology, Uppsala, Sweden) equilibrated with 50 mM potassium phosphate buffer pH 6.7 containing 200 mM NaCl. The material from 1 L of culture medium was chromatographed separately in two samples on Sephacryl S-300 HR. Fractions, approximately 13 ml each, were eluted with 1500 ml of 50 mM potassium phosphate buffer containing 200 mM NaCl. The elution pattern for one sample is shown in FIG. 7 wherein the continuous graph denotes glucosidase activity, the bold dashed line denotes NAGase activity, the other dashed line denotes endochitinase activity, and the line made up of dots and dashes denotes chitobiosidase activity. A similar elution pattern was obtained for the second sample. The fractions of interest containing glucosidase activity (between the vertical lines in FIG. 7 and similar ones for the second sample) were pooled (approximately 230 ml) and concentrated to about 20 ml by transferring into dialysis tubing (6,000 to 8,000 Da cutoff) and concentrating 30–40-fold by placing the tubing in solid polyethylene glycol (35,000MW; Fluka Chemika, Buchs, Switzerland). The concentrated fractions were dialyzed overnight against a 20-fold volume of 25 mM Tris-$CH_3COOH$ buffer, pH 8.0. The sample was then applied to a chromatofocusing column (1×30 cm) packed with PBE 94 (Pharmacia LKB), and equilibrated with the same buffer used for dialysis. The column was eluted at a flow rate of 50 ml $h^{-1}$ with Polybuffer 96 (Pharmacia LKB), diluted 1:13 with water and adjusted to pH 7.0 with $CH_3COOH$ according to the manufacturer's directions. The elution pattern is shown in FIG. 8 wherein the continuous graph denotes glucosidase activity, the thicker dashed line denotes NAGase activity, the other dashed line denotes endochitinase activity, the bold line made up of dots and dashes denotes chitobiosidase activity and the other line made up of dots and dashes denotes pH. The fractions of interest (between the vertical bars in FIG. 8, fractions 13 to 16; 24 ml total) were pooled, dialyzed first against a 20-fold volume of 1M NaCl and then against a 40-fold volume distilled water to remove Polybuffer, and concentrated to a volume of 2 ml in a collodion bag system (10,000 Da cutoff; UH100/1, Schleicher & Schuell Inc., Keene, N.H.). As indicated in FIG. 8, these contained only glucosidase activity.

The results of the purification are summarized in Table 2 below. (The crude culture filtrate before dialysis is not listed because it contained reducing groups that interfered with the enzyme assay.)

The purified enzyme did not release p-nitrophenol from p-nitrophenyl-β-glucopyranoside under the assay conditions described above.

The purified enzyme was determined (by sodium dodecyl sulfate polyacrylamide gel electrophoresis after the protein was prepared under reducing conditions, from a regression based on the log of molecular weight of standard proteins as described above) to have a molecular mass of 78 kDa and was determined (by isoelectric focusing electrophoresis from a regression of distance versus isoelectric point of standard proteins as described above) to have an isoelectric point of 6.2.

The effect of pH on glucosidase activity (determined as described above) for the purified enzyme is shown by the graph in FIG. 5 defined by triangles.

The effect of temperature on glucosidase activity (determined as described above) for the purified enzyme is shown by the graph in FIG. 6 defined by triangles.

Example III

Synergistic Combinations

Assay mixtures were prepared that contained 20 μl of a conidial suspension (106 conidia/ml) of the test fungus, which was the plant pathogen Botrytis cinerea, potato dextrose broth (Difco Laboratories, Detroit, Mich.) made at 3 times the standard strength, and 20 μl of a solution of enzyme(s) to be tested (for controls, sterile water was substituted).

The enzyme solutions to be tested were made at 3 times the final concentration desired in the bioassay, and contained either a single enzyme or an equal part mixture of two, three or four different enzymes. Reaction mixtures were made in sterile Eppendorf tubes and the final pH was 5.0 to 5.5. Tubes were incubated at 25° C., and after 24–30 hours, the percentage of germinating conidia was determined (% of the first 100 spores seen on a microscope slide) and the length of 20 germ tubes was measured and averaged. All the enzyme treatments and the controls were performed simultaneously in a single experiment. Each experiment was repeated on two separate days and contained three treatment repetitions each time. The data sets from the two experiments were kept separated while data from the three treatment repetitions included in each experiment were combined and used for statistical analysis. For each treatment

TABLE 2

| Step | Total protein (mg) | Enzyme activity (nkatal) | Specific activity (nkatal $mg^{-1}$) | Purification (fold) | Yield (%) |
| --- | --- | --- | --- | --- | --- |
| Dialyzed Culture Filtrate | 450 | 1938 | 4.3 | 1.0 | 100 |
| Sephacryl S-300 HR | 144 | 907 | 6.3 | 1.5 | 47 |
| Chromatofocusing | 2.3 | 351 | 153 | 36 | 18 |

The concentrated peak fractions obtained as a result of the purification contained homogeneous glucan 1,3-β-glucosidase as shown by the presence of a single protein band upon SDS-PAGE and upon Native PAGE in a PhastGel system (Pharmacia LKB).

The enzyme shown no affinity to polyclonal antibodies prepared against the purified endochitinase or chitobiosidase from *Trichoderma harzianum* strain P1 having accession No. ATCC 74058.

with enzyme or enzymes, dosage response curves were obtained by probit analysis of the data. The lower and the upper 95% fiducial limits for 95% probability and $ED_{50}$ (dose effective for 50% inhibition) values for each enzyme and each combination of enzymes were also obtained by probit analysis.

The average value of spore germination and germ tube length of Botrytis cinerea under the conditions used were 70% and 425 μm in the absence of enzymes (control).

Percentage inhibition was calculated according to the following equation: %I=(1−%St/%Sc) ×100, wherein %I represents the percentage inhibition, %S$_t$ represents percentage germination of spores or germ tube length for the treatment of interest, and %S$_c$ represents the percentage of spores germinating or germ tube length for the control (no enzyme).

The enzymes used were the endochitinase, chitin 1,4-β-chitobiosidase, N-acetyl-β-glucosaminidase, and glucan 1,3-β-glucosidase isolated from *Trichoderma harzianum* strain P1 having accession No. 74058, described above.

The results are set forth in FIGS. 9–23 which are graphs of % inhibition vs. total enzyme(s) concentration wherein the graphs denoted by circles are for spore germination and the graphs denoted by triangles are for germ tube elongation and "Endoc" stands for the endochitinase, "Chitob" stands for the chitin 1,4-β-chitobiosidase, "NAG" stands for the N-acetyl-β-glucosaminidase, and "Glucos" stands for the glucan 1,3-β-glucosidase.

Figure 9:
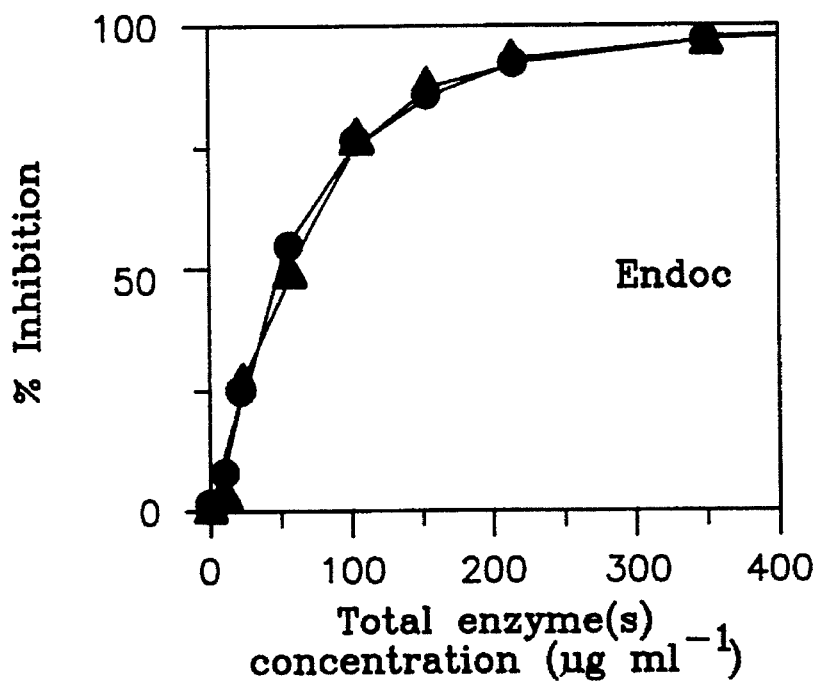
FIGS. 9–23 depict results of Example III.
Figure 10:
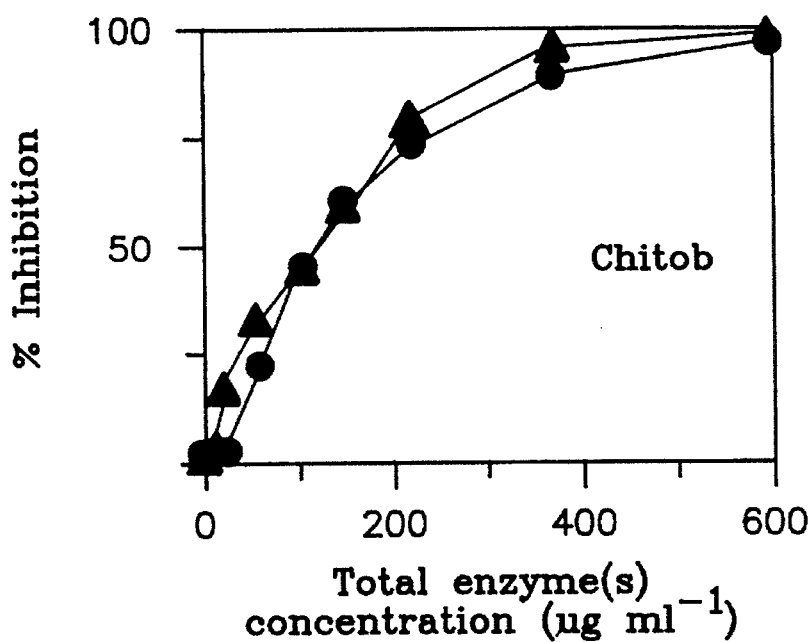
Figure 11:
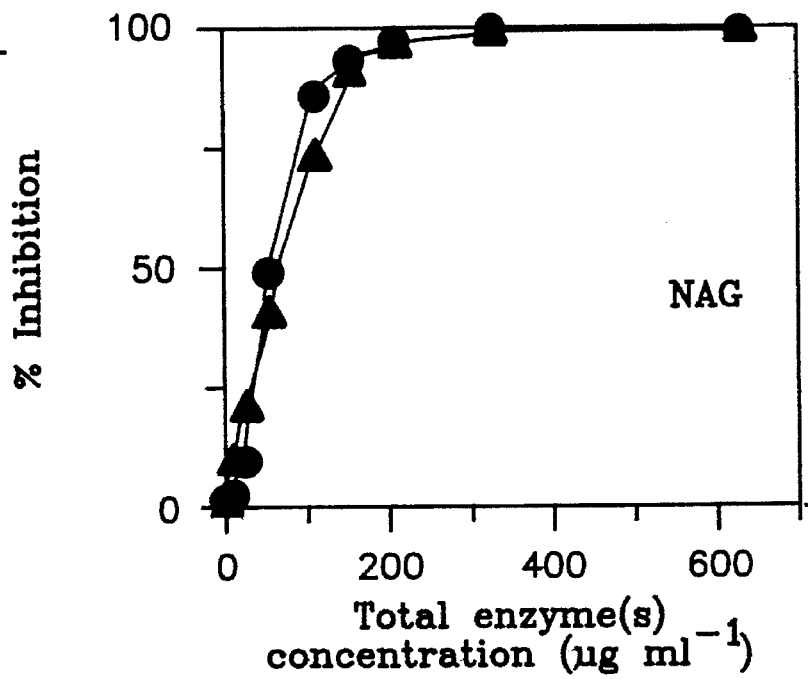
Figure 12:
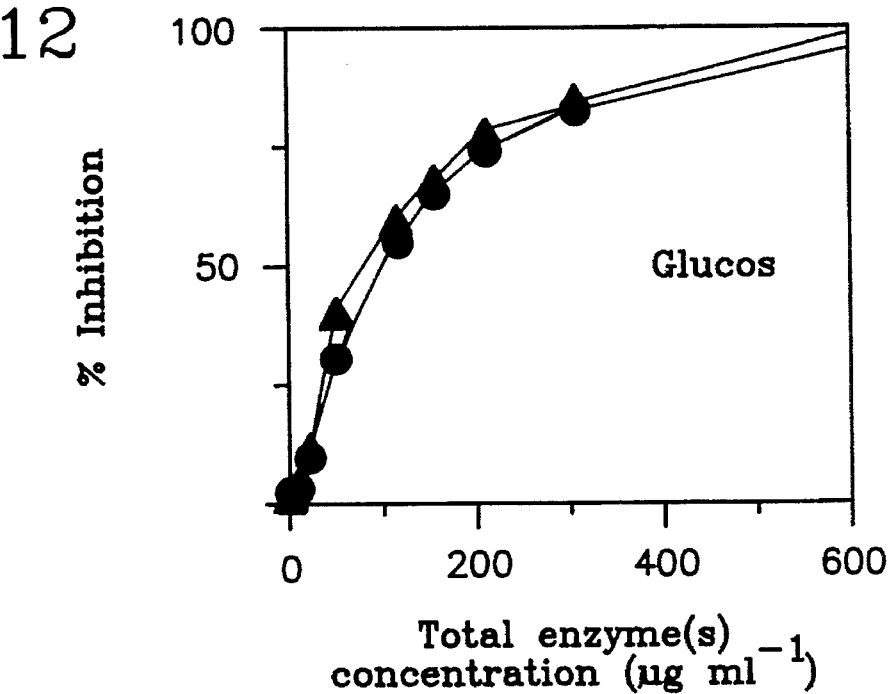
Figure 13:
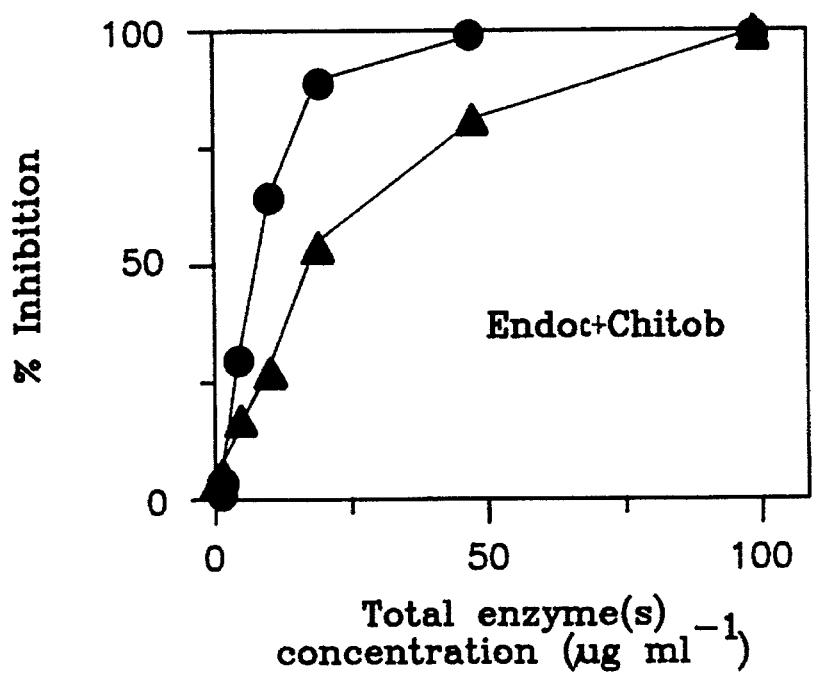
Figure 14:
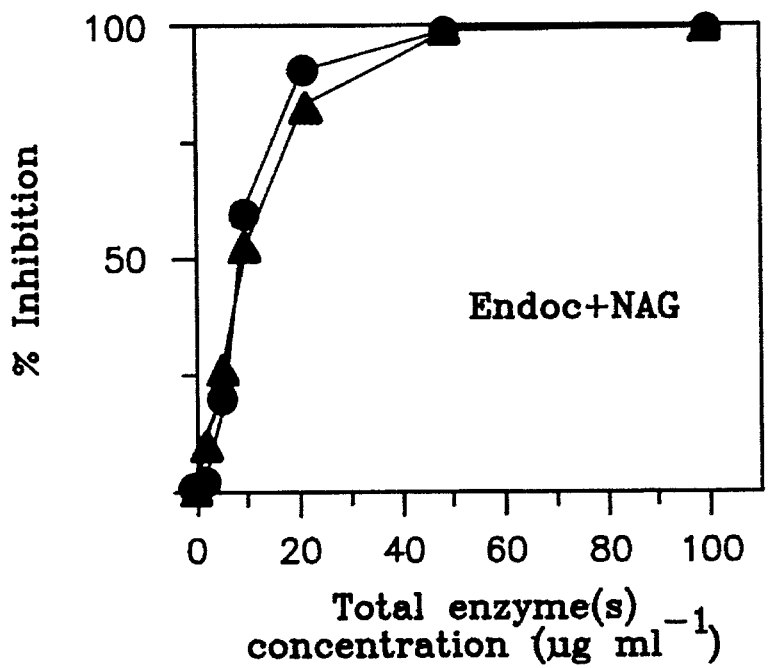
Figure 15:
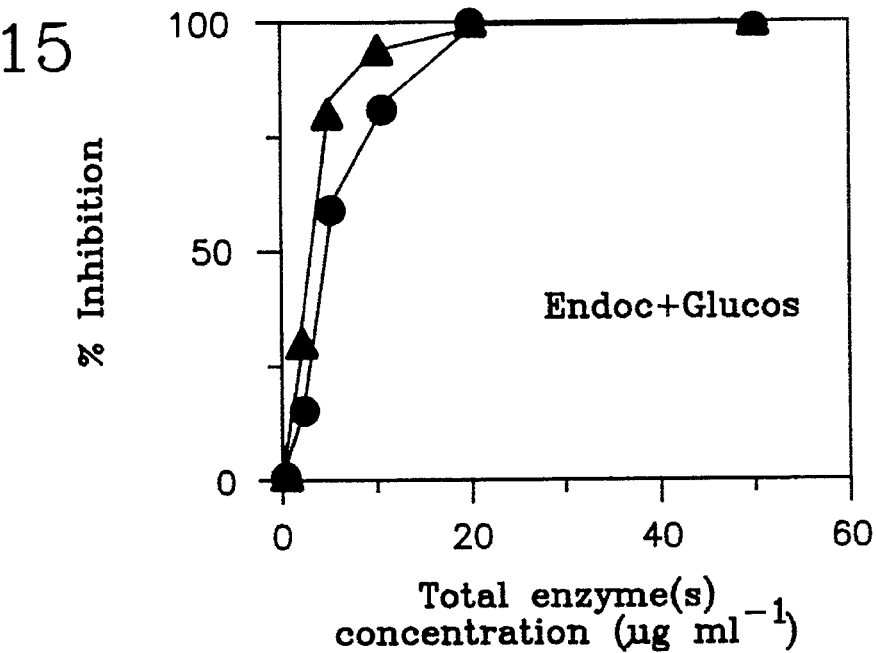
Figure 16:
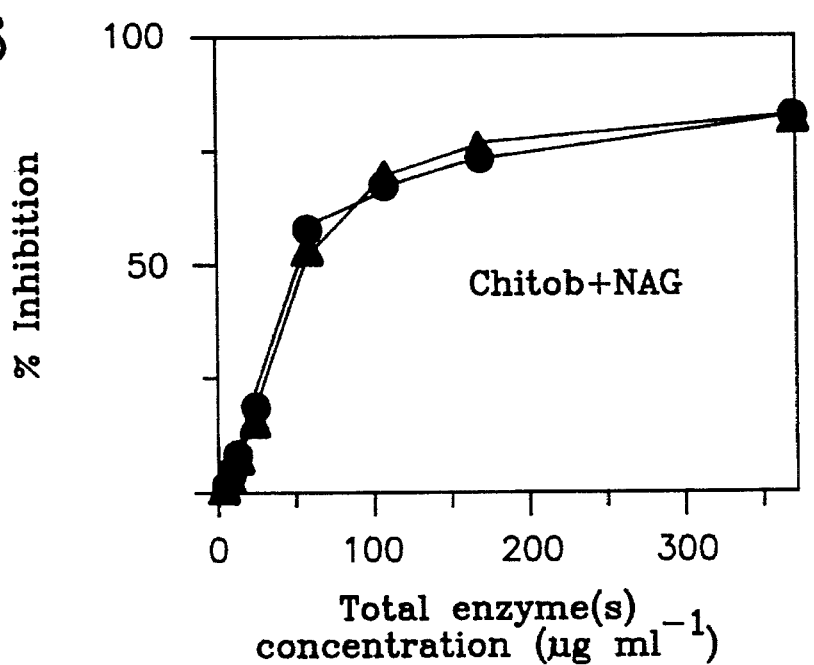
Figure 17:
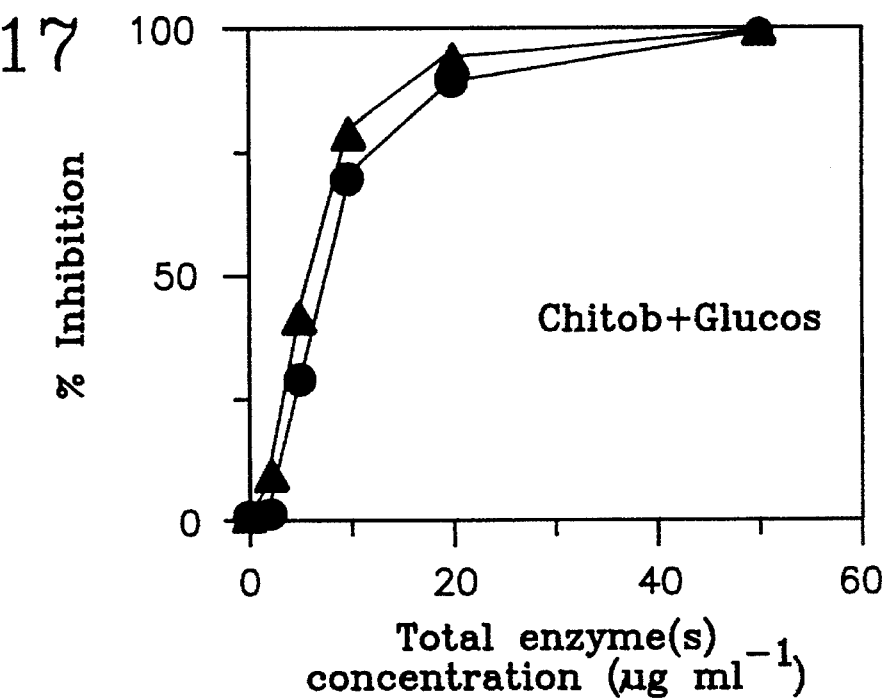
Figure 18:
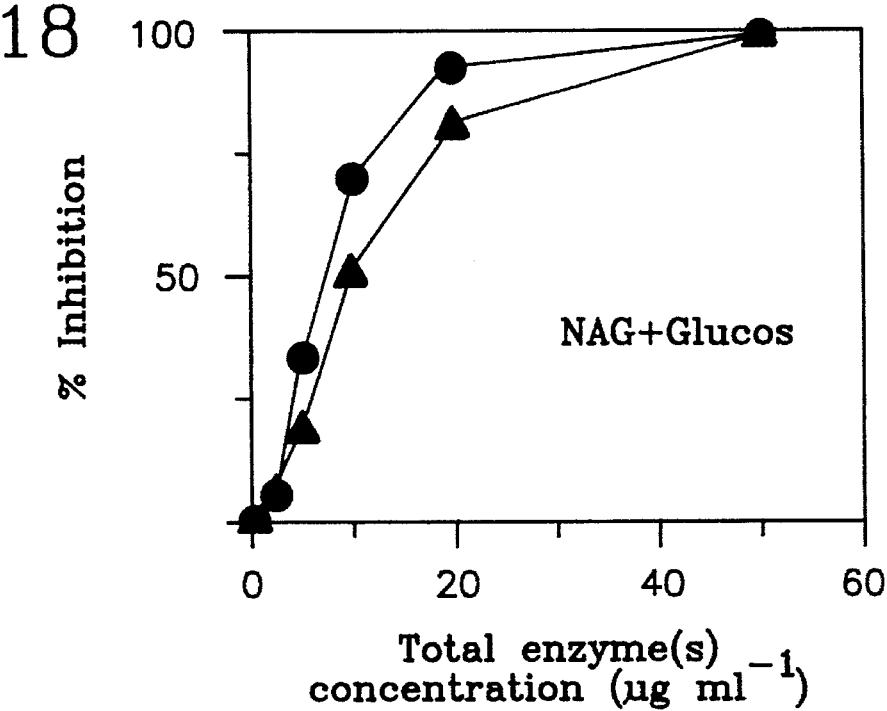
Figure 19:
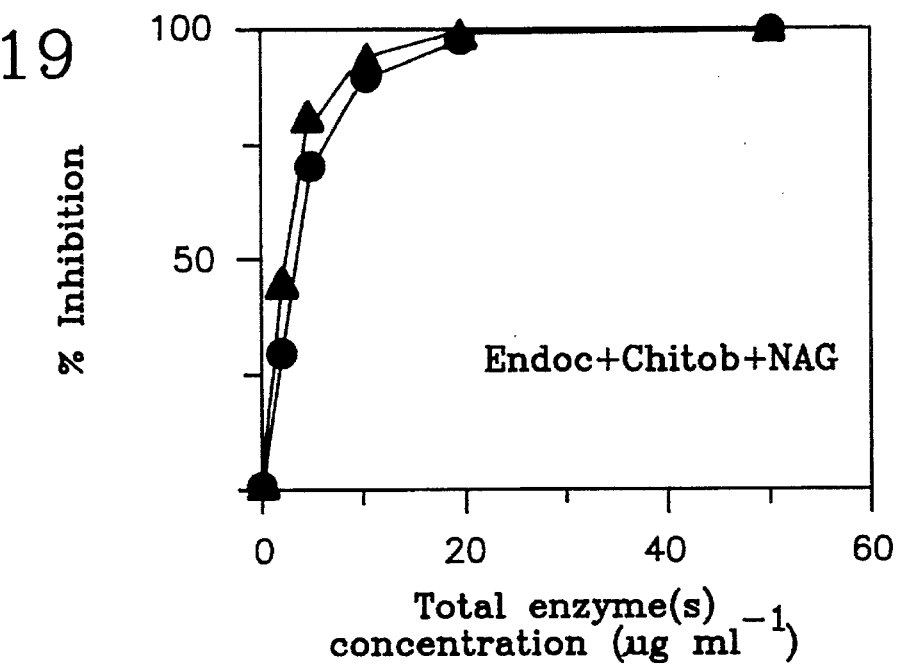
Figure 20:
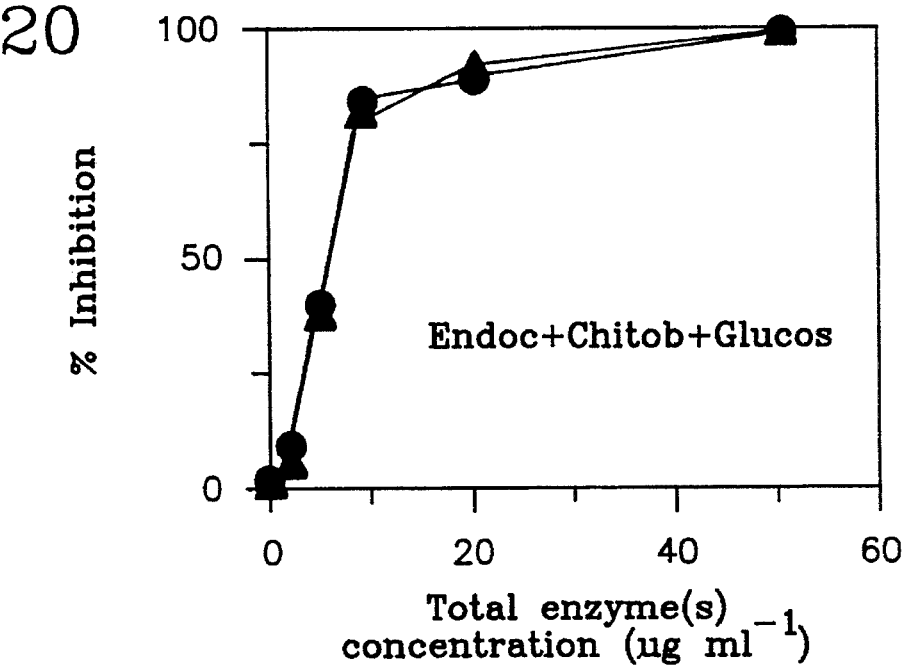
Figure 21:
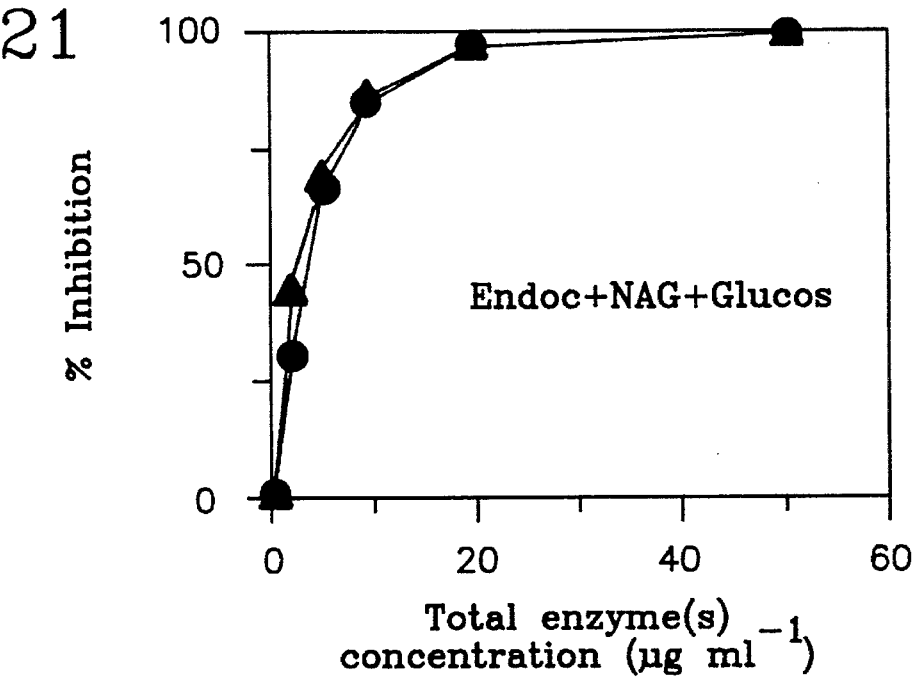
Figure 22:
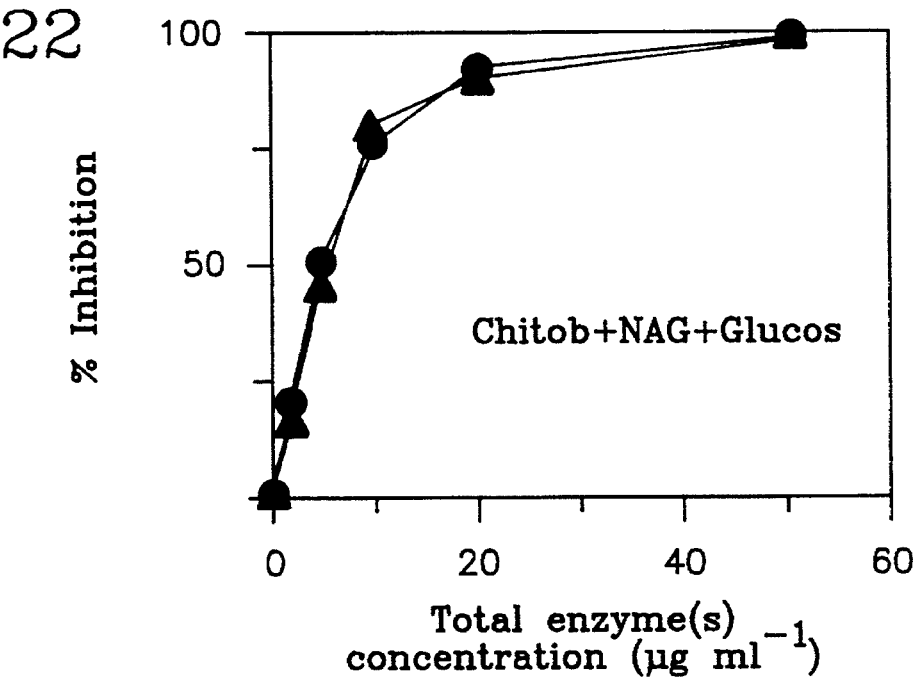
Figure 23:
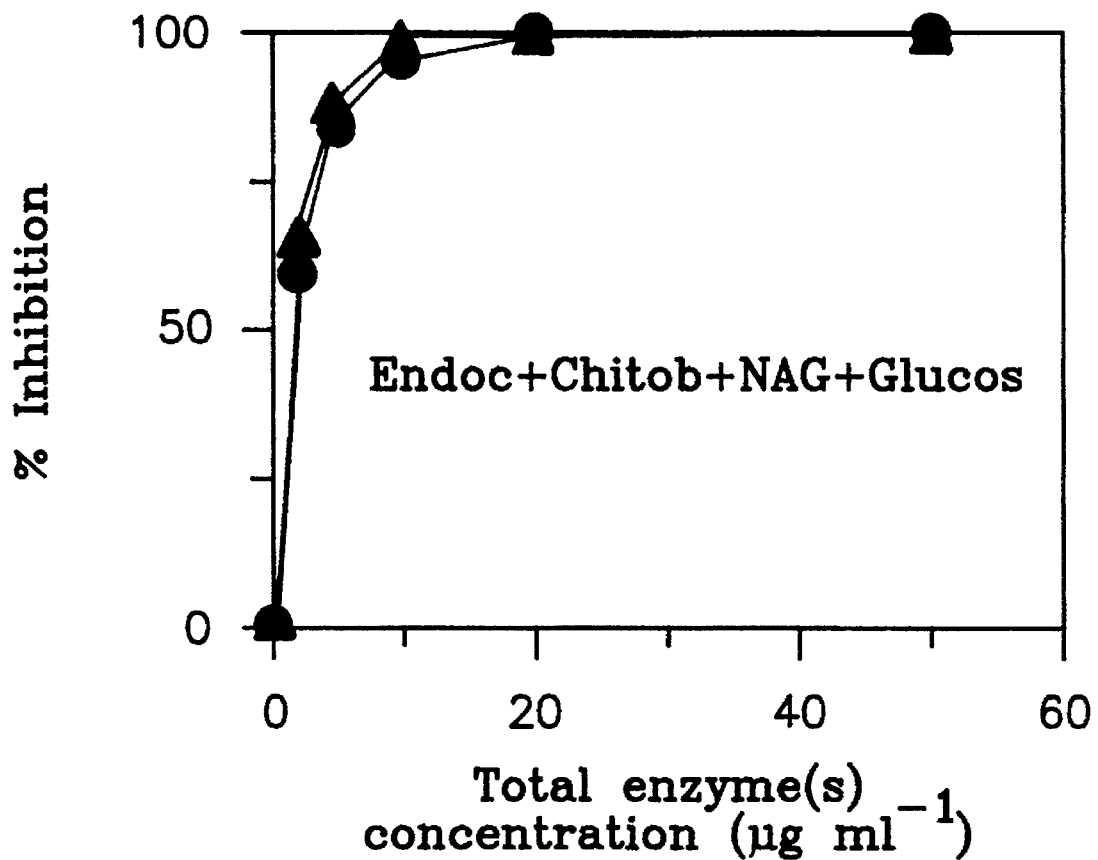

FIG. 9 sets forth results for the endochitinase. FIG. 10 sets forth the results for the chitin 1,4-β-chitobiosidase. FIG. 11 sets forth the results for the N-acetyl-β-glucosaminidase. FIG. 12 sets forth the results for the glucan 1,3-β-glucosidase. FIG. 13 sets forth the results for the endochitinase plus the chitin 1,4-β-chitobiosidase. FIG. 14 sets forth the results for the endochitinase plus the N-acetyl-β-glucosaminidase. FIG. 15 sets forth the results for the endochitinase plus the glucan 1,3-β-glucosidase. FIG. 16 sets forth the results for the chitin 1,4-β-chitobiosidase plus the N-acetyl-β-glucosaminidase. FIG. 17 sets forth the results for the chitin 1,4-β-chitobiosidase plus glucan 1,3-glucosidase. FIG. 18 sets forth the results for the N-acetyl-β-glucosaminidase plus the glucan 1,3-β-glucosidase. FIG. 19 sets forth the results for the endochitinase plus the chitin 1,4-β-chitobiosidase plus the N-acetyl-β-glucosaminidase. FIG. 20 sets forth the results for the endochitinase plus the chitin 1,4-β-chitobiosidase plus the glucan 1,3-β-glucosidase. FIG. 21 sets forth the results for the endochitinase plus the N-acetyl-β-glucosaminidase plus the glucan 1,3-β-glucosidase. FIG. 22 sets forth the results for the chitin 1,4-β-chitobiosidase plus the N-acetyl-β-glucosaminidase plus the N-acetyl-β-glucosaminidase plus the glucan 1,3-β-glucosidase. FIG. 23 sets forth the results for the endochitinase plus the chitin 1,4-β-chitobiosidase plus the N-acetyl-β-glucosaminidase plus the glucan 1,3-β-glucosidase.

As indicated by FIGS. 9–12, 200–600 μg ml$^{-1}$ were needed for complete inhibition when the enzymes were tested singly. As indicated by FIGS. 13–18, 20 to 100 μg ml$^{-1}$ were needed for complete inhibition for binary combinations except in the case of the NAGase plus gluconase. As indicated in FIGS. 19–22, 20 to 50 μg ml$^{-1}$ were needed for complete inhibition for ternary combinations. As indicated in FIG. 23, 10 and 20 μg ml$^{-1}$ were needed for complete inhibition for the quaternary combination.

Table 3 below shows ED$_{50}$ (dose effective for 50% inhibition) for the enzymes alone and in combination.

TABLE 3

| Enzyme | ED$_{50}$ (μg ml$^{-1}$) Germination Inhibition | ED$_{50}$ (μg ml$^{-1}$) Germ Tube Elongation Inhibition |
|---|---|---|
| Endochitinase | 47.5 (45–49) | 53 (49–55) |
| Chitobiosidase | 117 (112–121) | 125 (115–133) |
| NAGase | 51 (49.9–52.8) | 70 (63–75) |
| Glucosidase | 94.5 (90–99) | 90 (86–96) |
| Endochitinase plus Chitobiosidase | 7.8 (7.5–8.2) | 19 (16.5–22) |
| Endochitinase plus NAGase | 8.8 (8.5–9.2) | 9.5 (8–11) |
| Endochitinase plus Glucosidase | 4.5 (4.3–4.7) | 3.5 (2.8–4) |
| Chitobiosidase plus NAGase | 44 (41–47) | 48 (44–51) |
| Chitobiosidase plus Glucosidase | 6.4 (6.2–6.6) | 9 (8–9.9) |
| NAGase plus Glucosidase | 7.1 (6.8–7.5) | 8 (7.2–9) |
| Endochitinase plus Chitobiosidase plus NAGase | 6.7 (6.3–7) | 6 (5.4–6.8) |
| Endochitinase plus Chitobiosidase plus Glucosidase | 3.2 (3–3.4) | 2.5 (2–3) |
| Endochitinase plus NAGase plus Glucosidase | 3.5 (3.3–3.7) | 5 (4.2–5.5) |
| Chitobiosidase plus NAGase plus Glucosidase | 5.1 (4.8–5.4) | 7 (5.8–7.9) |
| Endochitinase plus Chitobiosidase plus NAGase plus Glucosidase | 1.6 (1.5–1.7) | 1.7 (1.5–2) |

Table 4 below shows the percent inhibition of spore germination and germ tube elongation provided by 50 μg/ml of total enzyme as set forth.

TABLE 4

| | Inhibition of Germination @ 50 μg/ml | Inhibition of Germ Tube Elongation @ 50 μg/ml |
|---|---|---|
| Endochitinase | 44 | 43 |
| Chitobiosidase | 21 | 25 |
| NAGase | 42 | 42 |
| Glucosidase | 28 | 32 |
| Endochitinase plus Chitobiosidase | 90 | 81 |
| Endochitinase plus NAGase | 93 | 100 |
| Endochitinase plus Glucosidase | 100 | 100 |
| Chitobiosidase plus Nagase | 48 | 45 |
| Chitobiosidase plus Glucosidase | 100 | 83 |

TABLE 4-continued

|  | Inhibition of Germination @ 50 μg/ml | Inhibition of Germ Tube Elongation @ 50 μg/ml |
| --- | --- | --- |
| NAGase plus Glucosidase | 100 | 85 |
| Endochitinase plus Chitobiosidase plus NAGase | 96 | 100 |
| Endochitinase plus Chitobiosidase plus Glucosidase | 100 | 99 |
| Endochitinase plus NAGase plus Glucosidase | 100 | 100 |
| Chitobiosidase plus NAGase plus Glucosidase | 100 | 89 |
| Endochitinase plus Chitobiosidase plus NAGase plus Glucosidase | 92 | 96 |

The synergy of the various combinations in all cases is demonstrated according to the formula in Richter, D. L., Pestic. Sci. 19:309–315, 1987. In accordance with that formula, if synergism exists $E_o(xA+yB+\ldots nN) > E_o(x+y+\ldots n)A$, $> E_o(x+y+\ldots n)B \ldots$ and $> E_o(x+y+\ldots n)N$, where $E_o$ is the percentage inhibition, A, B, N are the compounds tested and x,y, ... n are the concentrations of each compound. Table 4 shows synergy for all combinations since 50 μg/ml of each combination is shown to provide greater inhibition than 50 μg/ml of each component thereof.

Variations in the invention will be obvious to those skilled in the art. Therefore, the invention is defined by the claims.

What is claimed is:

1. An essentially pure enzyme having N-acetyl-β-glucosaminidase activity, which is derived from *Trichoderma harzianum* strain P1 ATCC 74058 and which has a molecular mass of 72 kDa as determined by sodium dodecyl sulfate polyacrylamide gel electrophoresis after the enzyme was prepared under reducing conditions, from a regression based on the log of molecular weight of standard proteins, and an isoelectric point of 4.6 as determined by isoelectric focusing electrophoresis from a regression of distance versus isoelectric point of standard proteins.

* * * * *